(12) United States Patent
Whitman et al.

(10) Patent No.: US 8,960,519 B2
(45) Date of Patent: Feb. 24, 2015

(54) SHAFT, E.G., FOR AN ELECTRO-MECHANICAL SURGICAL DEVICE

(75) Inventors: Michael P. Whitman, New Hope, PA (US); Donald T. Malinouskas, Monroe, CT (US)

(73) Assignee: Covidien LP, Mansfield, MA (US)

( * ) Notice: Subject to any disclaimer, the term of this patent is extended or adjusted under 35 U.S.C. 154(b) by 908 days.

(21) Appl. No.: 11/495,920

(22) Filed: Jul. 27, 2006

(65) Prior Publication Data
US 2007/0055219 A1    Mar. 8, 2007

Related U.S. Application Data

(63) Continuation-in-part of application No. 10/099,634, filed on Mar. 15, 2002, now Pat. No. 7,951,071, which is a continuation-in-part of application No. 09/887,789, filed on Jun. 22, 2001, now Pat. No.
(Continued)

(51) Int. Cl.
*A61B 17/04* (2006.01)
*A61B 10/04* (2006.01)
(Continued)

(52) U.S. Cl.
CPC ......... *A61B 17/00234* (2013.01); *A61B 17/068* (2013.01); *A61B 17/115* (2013.01);
(Continued)

(58) Field of Classification Search
CPC ............ A61B 1/01; A61B 1/05; A61B 1/018; A61B 1/00098; A61B 1/31; A61B 1/00082; A61B 1/041; A61B 1/0052; A61B 1/00112; A61B 1/0058; A61B 5/06; A61B 17/07207; A61B 17/0684; A61B 17/115; A61B 17/072; A61B 17/068; A61B 2019/4873; B23C 1/06; B27M 3/36; B27F 7/19; B25C 1/04; B25C 5/0228

USPC ......... 600/114, 175, 117, 160, 178, 182, 101, 600/103, 104, 106, 107, 115, 118, 136, 137, 600/145; 356/619, 419; 227/2–7, 227/751.1–751.4, 176.1, 177.1, 178.1, 227/179.1, 180.1, 181.1, 182.1; 606/1, 606/139–159

See application file for complete search history.

(56) References Cited

U.S. PATENT DOCUMENTS 4,162,399 A    7/1979  Hudson
4,823,807 A *  4/1989  Russell et al. ................. 600/586
(Continued)

FOREIGN PATENT DOCUMENTS

CA        2451558        1/2003
CN      102 247 182    11/2011
(Continued)

OTHER PUBLICATIONS

European Search Report for corresponding EP06788914 date of mailing is May 11, 2012 (8 pgs).
(Continued)

*Primary Examiner* — Ryan Henderson

(57) ABSTRACT

A shaft being, e.g., flexible, that includes an elongated outer sheath, at least one drive shaft disposed within the outer sheath and a ring non-rotatably mounted on the at least one rotatable drive shaft and at least one light source mounted within the shaft, such that, upon rotation of the at least one rotatable drive shaft, the ring alternately blocks and allows light from the light source to be detected. The shaft may also include a moisture sensor disposed within the outer sheath of the shaft and configured to detect moisture within the outer sheath. The shaft may include couplings that connect a distal end of the outer sheath to a surgical attachment and a proximal end of the outer sheath to a remote power console.

20 Claims, 18 Drawing Sheets

Related U.S. Application Data 7,032,798, which is a continuation-in-part of application No. 09/836,781, filed on Apr. 17, 2001, now Pat. No. 6,981,941, which is a continuation-in-part of application No. 09/723,715, filed on Nov. 28, 2000, now Pat. No. 6,793,652, which is a continuation-in-part of application No. 09/324,451, filed on Jun. 2, 1999, now Pat. No. 6,315,184, and a continuation-in-part of application No. 09/324,452, filed on Jun. 2, 1999, now Pat. No. 6,443,973, and a continuation-in-part of application No. 09/351,534, filed on Jul. 12, 1999, now Pat. No. 6,264,087, and a continuation-in-part of application No. 09/510,923, filed on Feb. 22, 2000, now Pat. No. 6,517,565, which is a continuation-in-part of application No. 09/324,452, and a continuation-in-part of application No. 09/510,927, filed on Feb. 22, 2000, now Pat. No. 6,716,233, which is a continuation-in-part of application No. 09/324,452, and a continuation-in-part of application No. 09/510,932, filed on Feb. 22, 2000, now Pat. No. 6,491,201.

(60) Provisional application No. 60/703,227, filed on Jul. 27, 2005.

(51) Int. Cl.
*A61B 1/04* (2006.01)
*A61B 17/00* (2006.01)
*A61B 17/068* (2006.01)
*A61B 17/115* (2006.01)
*A61B 17/128* (2006.01)
*A61B 17/72* (2006.01)
*A61B 19/00* (2006.01)
*A61B 17/29* (2006.01)

(52) U.S. Cl.
CPC ......... *A61B17/1285* (2013.01); *A61B 17/7208* (2013.01); *A61B 19/22* (2013.01); *A61B 19/44* (2013.01); *A61B 2017/00026* (2013.01); *A61B 2017/00119* (2013.01); *A61B 2017/00199* (2013.01); *A61B 2017/00398* (2013.01); *A61B 2017/00464* (2013.01); *A61B 2017/00853* (2013.01); *A61B 2017/2905* (2013.01); *A61B 2019/2242* (2013.01); *A61B 2019/2276* (2013.01); *A61B 2019/467* (2013.01); *A61B 2019/4815* (2013.01); *A61B 2019/4857* (2013.01); *A61B 2019/5206* (2013.01); *A61B 2217/005* (2013.01)
USPC .................. 227/175.1; 227/176.1; 227/181.1; 600/117; 600/118; 606/1

(56) References Cited

U.S. PATENT DOCUMENTS

| | | | |
|---|---|---|---|
| 5,693,042 | A | 12/1997 | Boiarski et al. |
| 7,147,138 | B2 | 12/2006 | Shelton |
| 7,947,034 | B2 | 5/2011 | Whitman |
| 8,114,118 | B2 | 2/2012 | Knodel et al. |
| 8,182,494 | B1 | 5/2012 | Yencho et al. |
| 8,292,150 | B2 | 10/2012 | Bryant |
| 8,517,241 | B2 | 8/2013 | Nicholas et al. |
| 2002/0049454 | A1 | 4/2002 | Whitman |
| 2003/0038938 | A1* | 2/2003 | Jung et al. .............. 356/419 |
| 2004/0111012 | A1* | 6/2004 | Whitman ............... 600/179 |
| 2004/0111081 | A1* | 6/2004 | Whitman et al. ............ 606/1 |
| 2006/0278680 | A1 | 12/2006 | Viola et al. |
| 2007/0023477 | A1 | 2/2007 | Whitman et al. |
| 2007/0055219 | A1 | 3/2007 | Whitman et al. |
| 2007/0152014 | A1 | 7/2007 | Gillum et al. |
| 2007/0175961 | A1 | 8/2007 | Shelton et al. |
| 2008/0110958 | A1 | 5/2008 | McKenna et al. |
| 2008/0255413 | A1 | 10/2008 | Zemlok et al. |
| 2009/0090763 | A1 | 4/2009 | Zemlok et al. |
| 2009/0254094 | A1 | 10/2009 | Knapp et al. |
| 2010/0225073 | A1 | 9/2010 | Porter et al. |
| 2011/0077673 | A1 | 3/2011 | Grubac et al. |
| 2011/0125138 | A1 | 5/2011 | Malinouskas et al. |
| 2011/0139851 | A1 | 6/2011 | McCuen |
| 2011/0155783 | A1 | 6/2011 | Rajappa et al. |
| 2011/0174099 | A1 | 7/2011 | Ross et al. |
| 2011/0204119 | A1 | 8/2011 | McCuen |
| 2011/0290854 | A1 | 12/2011 | Timm et al. |
| 2011/0295242 | A1 | 12/2011 | Spivey et al. |
| 2011/0295269 | A1 | 12/2011 | Swensgard et al. |
| 2012/0000962 | A1 | 1/2012 | Racenet et al. |
| 2012/0089131 | A1 | 4/2012 | Zemlok et al. |
| 2012/0143002 | A1 | 6/2012 | Aranyi et al. |
| 2012/0223121 | A1 | 9/2012 | Viola et al. |
| 2012/0253329 | A1 | 10/2012 | Zemlok et al. |
| 2012/0310220 | A1 | 12/2012 | Malkowski et al. |
| 2012/0323226 | A1 | 12/2012 | Chowaniec et al. |
| 2013/0018361 | A1 | 1/2013 | Bryant |
| 2013/0098966 | A1 | 4/2013 | Kostrzewski et al. |
| 2013/0098968 | A1 | 4/2013 | Aranyi et al. |
| 2013/0098969 | A1 | 4/2013 | Scirica et al. |
| 2013/0214025 | A1 | 8/2013 | Zemlok et al. |
| 2013/0240596 | A1 | 9/2013 | Whitman |
| 2013/0274722 | A1 | 10/2013 | Kostrzewski et al. |
| 2013/0282052 | A1 | 10/2013 | Aranyi et al. |

FOREIGN PATENT DOCUMENTS

| | | | |
|---|---|---|---|
| DE | 102008053842 A1 | | 5/2010 |
| EP | 0648476 A1 | | 4/1995 |
| EP | 0686374 A2 | | 12/1995 |
| EP | 1813199 | | 8/2007 |
| EP | 1813211 | | 8/2007 |
| EP | 2 005 898 | | 12/2008 |
| EP | 2165664 A2 | | 3/2010 |
| EP | 2236098 | | 10/2010 |
| EP | 2263568 | | 12/2010 |
| EP | 2329773 | | 6/2011 |
| EP | 2333509 A1 | | 6/2011 |
| EP | 2462880 A2 | | 6/2012 |
| EP | 2491872 A1 | | 8/2012 |
| EP | 2586382 | | 5/2013 |
| EP | 2606834 | | 6/2013 |
| EP | 2676615 A2 | | 12/2013 |
| WO | WO 03/000138 | | 1/2003 |
| WO | WO 03/077769 A1 | | 9/2003 |
| WO | WO 2011/108840 | | 9/2011 |

OTHER PUBLICATIONS

Extended European Search Report corresponding to EP No. 11 17 8021.9, mailed Jun. 4, 2013; (3 pp).
Extended European Search Report corresponding to EP No. 13 16 3033.7, completed Jun. 27, 2013 and mailed Jul. 15, 2013; (8 pp).
Extended European Search Report corresponding to EP No. 12 18 6177.7, completed Aug. 14, 2013 and mailed Aug. 23, 2013; (8 pp).
Partial European Search Report corresponding to EP No. 13 17 1742.3, completed Sep. 17, 2013 and mailed Sep. 25, 2013; (8 pp).
Partial European Search Report corresponding to EP No. 13 17 2400.7, completed Sep. 18, 2013 and mailed Oct. 1, 2013; (7 pp).
Extended European Search Report corresponding to EP No. 13 17 5475.6, completed Sep. 23, 2013 and mailed Oct. 1, 2013; (8 pp).
Extended European Search Report corresponding to EP No. 13 17 5478.0, completed Sep. 24, 2013 and mailed Oct. 2, 2013; (6 pp).
Extended European Search Report corresponding to EP No. 13 17 5479.8, completed Sep. 27, 2013 and mailed Oct. 10, 2013; (7 pp).
Partial Extended European Search Report corresponding to EP 13 17 5477.2, completed Oct. 7, 2013 and mailed Oct. 15, 2013; (7 pp).
Extended European Search Report corresponding to EP No. 08 25 2703.7, completed Oct. 23, 2008 and mailed Oct. 31, 2008; (7 pp).
European search Report from Appl. No. 13177163.6 dated Nov. 15, 2013. (8 pp).

(56) References Cited

OTHER PUBLICATIONS

Extended European Search Report from Application No. EP 13175477.2 dated Feb. 6, 2014.
Extended European Search Report from EP Application No. 13172400.7 dated Jan. 21, 2014.
Extended European Search Report from Application No. EP 13169998.5 dated Feb. 24, 2014.
The extended European Search Report from Application No. EP 13177163.6 dated Feb. 6, 2014.
Extended European Search Report corresponding to EP 13176805.3, dated Nov. 4, 2013.
Extended European Search Report from EP Application No. 13189026.1 dated Jan. 31, 2014.
Extended European Search Report from Application No. EP 13171742.3 dated Jan. 3, 2014.

* cited by examiner

SHAFT, E.G., FOR AN ELECTRO-MECHANICAL SURGICAL DEVICE

CROSS-REFERENCE TO RELATED APPLICATIONS

This application claims the benefit of U.S. Provisional Patent. Application No. 60/703,227, entitled "Flexible Shaft, e.g., for an Electro-Mechanical Surgical Device", filed on Jul. 27, 2005, which is expressly incorporated herein in its entirety by reference hereto.

This application is also a continuation-in-part of U.S. patent application Ser. No. 10/099,634, filed on Mar. 15, 2002 now U.S. Pat. No. 7,951,071, which is a continuation-in-part of U.S. patent application Ser. No. 09/887,789, filed on Jun. 22, 2001, now U.S. Pat. No. 7,032,798, which is a continuation-in-part of U.S. patent application Ser. No. 09/836,781, filed on Apr. 17, 2001, now U.S. Pat. No. 6,981,941, which is a continuation-in-part of U.S. Pat. application No. 09/723,715, filed on Nov. 28, 2000, now U.S. Pat. No. 6,793,652, which is a continuation-in-part of U.S. patent application Ser. No. 09/324,451, filed on Jun. 2, 1999, now U.S. Pat. No. 6,315,184, a continuation-in-part of U.S. patent application Ser. No. 09/324,452, filed on Jun. 2, 1999, now U.S. Pat. No. 6,443,973. a continuation-in-part of U.S. patent application Ser. No. 09/351,534, filed on Jul. 12, 1999, now U.S. Pat. No. 6,264,087, a continuation-in-part of U.S. patent application Ser. No. 09/510,923, filed on Feb. 22, 2000, now U.S. Pat. No. 6,517,565, which is a continuation-in-part of U.S. patent application Ser. No. 09/324,452 filed on Jun. 2, 1999, now U.S. Pat. No. 6,443,973, a continuation-in-part of U.S. patent application Ser. No. 09/510,927, filed on Feb. 22, 2000, now U.S. Pat. No. 6,716,233, which is a continuation-in-part of U.S. patent application Ser. No. 09/324,452, now U.S. Pat. No. 6,443,973, a continuation-in-part of U.S. patent application Ser. No. 09/510,932, filed on Feb. 22, 2000, now U.S. Pat. No. 6,491,201.

FIELD OF THE INVENTION

The present invention relates to a shaft, and more particularly, to a shaft for use with an electromechanical surgical device.

BACKGROUND INFORMATION

Various surgical systems are known. For instance, a surgical system may include an electromechanical driver device detachably coupled to a surgical attachment. Such an electromechanical driver device is described in, for example, U.S. patent application Ser. No. 09/723,715, entitled "Electro-Mechanical Surgical Device," filed on Nov. 28, 2000, now issued as U.S. Pat. No. 6,793,652, U.S. patent application Ser. No. 09/836,781, entitled "Electro-Mechanical Surgical Device, filed on Apr. 17, 2001, and U.S. patent application Ser. No. 09/887,789, entitled "Electro-Mechanical Surgical Device," filed on Jun. 22, 2001, each of which is expressly incorporated herein in its entirety by reference. Certain surgical instruments and systems described may suffer numerous disadvantages, as set forth in additional detail below. Generally, conventional surgical systems may include shafts that provide limited torque, may not provide a user to accurately ascertain the positions of the operative elements of associated instruments and systems, may not provide moisture detection capabilities, and may be generally complicated and expensive to assemble.

SUMMARY

In an example embodiment of the present invention, a flexible shaft for coupling a surgical attachment with an electromechanical driver device is provided that includes a flexible, elongated outer sheath, the sheath being formed from an autoclavable material, and at least one drive shaft disposed in the outer sheath. In an example embodiment of the present invention, the flexible shaft includes a moisture sensor disposed within the outer sheath configured to detect moisture within the flexible outer sheath. The flexible shaft may also include one or more rotatable drive shafts that are connected to drive shafts of a motor system of the electromechanical driver device so as to rotate and thereby operate a surgical attachment. Each one of the rotatable drive shafts of the flexible shaft may include a tabbed quadrature ring that alternately blocks and allows light from a light source to be conveyed via fiber optic cables to a controller that is configured to detect and interpret the light signals received via the fiber optic cables and to determine, e.g., the position and/or direction of a component, e.g., an anvil or cutting blade, of the surgical attachment, e.g., a surgical stapler, in response thereto. The flexible shaft may further include additional channels for providing irrigation and/or aspiration to a surgical site via the flexible shaft.

In an example embodiment of the present invention, a shaft includes: an elongated outer sheath; at least one rotatable drive shaft disposed within the outer sheath; a member extending radially from and configured to rotate with the at least one rotatable drive shaft; and at least one light source mounted within the outer sheath, wherein, upon rotation of the at least one rotatable drive shaft, the member alternately blocks and allows light from the light source to be detected. The member may be a tab, e.g., or two tabs that extend from a quadrature ring mounted on the at least one rotatable drive shaft. Also, there may be provided two light sources mounted at a distal end of the shaft, for example, mounted about 90 degrees from to each other relative to an axis of the at least one rotatable drive shaft.

DETAILED DESCRIPTION

Figure 1:
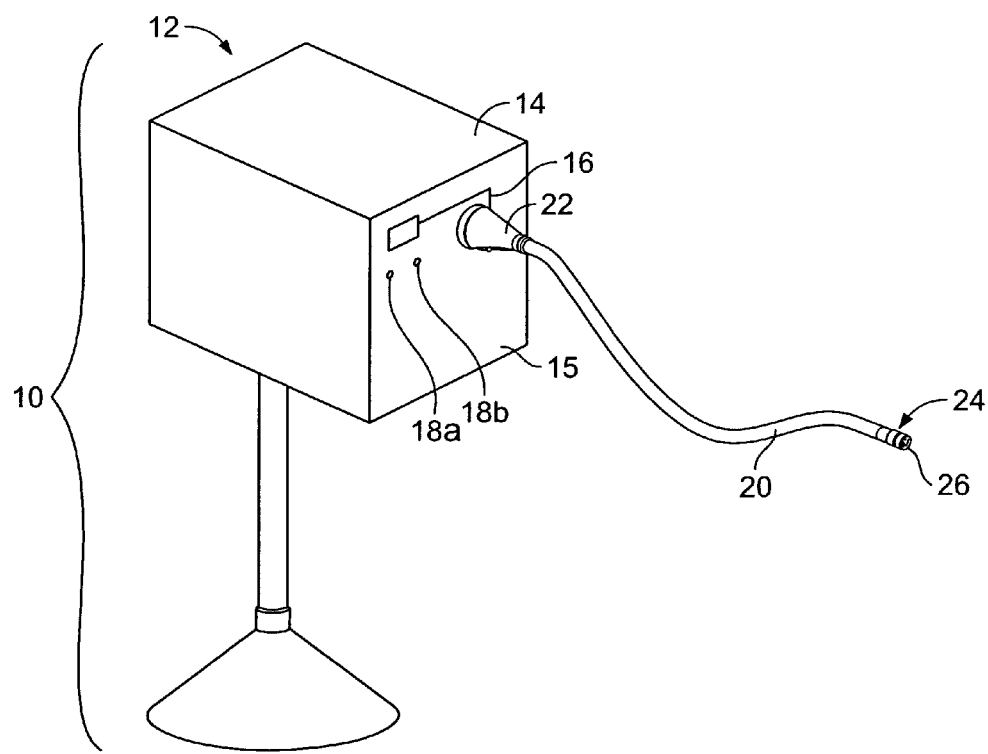
FIG. 1 is a perspective view of an electromechanical surgical device according to an example embodiment of the present invention.

Referring to FIG. 1, there is seen a perspective view of an electromechanical surgical device 10 according to an example embodiment of the present invention. The electromechanical surgical device 10 may include, for example, a remote power console 12, which includes a housing 14 having a front panel 15. Mounted on the front panel 15 are a display device 16 and indicators 18a, 18b, which are more fully described hereinbelow. A shaft 20 may extend from the housing 14 and may be detachably secured thereto via a first coupling 22. The shaft 20 may be flexible, rigid, articulable, articulatable, etc. Although the shaft 20 is referred to below as a flexible shaft 20, it should be understood that reference to a flexible shaft 20 is merely one example embodiment of the shaft 20 and that the shaft 20 is in no way limited to a flexible arrangement. The distal end 24 of the flexible shaft 20 may include a second coupling 26 adapted to detachably secure a surgical instrument or attachment to the distal end 24 of the flexible shaft 20. The surgical instrument or attachment may be, for example, a surgical stapler, a surgical cutter, a surgical stapler-cutter, a linear surgical stapler, a linear surgical stapler-cutter, a circular surgical stapler, a circular surgical stapler-cutter, a surgical clip applier, a surgical clip ligator, a surgical clamping device, a vessel expanding device, a lumen expanding device, a scalpel, a fluid delivery device or any other type of surgical instrument. Such surgical instruments are described, for example, in U.S. patent application Ser. No. 09/324,451, entitled "A Stapling Device for Use with an Electromechanical Driver Device for Use with Anastomosing, Stapling, and Resecting Instruments," now issued as U.S. Pat. No. 6,315,184, U.S. patent application Ser. No. 09/324,452, entitled "Electromechanical Driver Device for Use with Anastomosing, Stapling, and Resecting Instruments," now issued as U.S. Pat. No. 6,443,973, U.S. patent application Ser. No. 09/351,534, entitled "Automated Surgical Stapling System," now issued as U.S. Pat. No. 6,264,087, U.S. patent application Ser. No. 09/510,926, entitled "A Vessel and Lumen Expander Attachment for Use with an Electromechanical Driver Device," now issued as U.S. Pat. No. 6,348,061, U.S. patent application Ser. No. 09/510,927, entitled "Electromechanical Driver and Remote Surgical Instruments Attachment Having Computer Assisted Control Capabilities," now issued as U.S. Pat. No. 6,716,233, U.S. patent application Ser. No. 09/510,931, entitled "A Tissue Stapling Attachment for Use with an Electromechanical Driver Device," now issued as U.S. Pat. No. 6,533,157, U.S. patent application Ser. No. 09/510,932, entitled "A Fluid Delivery Mechanism for Use with Anastomosing, Stapling, and Resecting Instruments," now issued as U.S. Pat. No. 6,491,201, and U.S. patent application Ser. No. 09/510,933, entitled "A Fluid Delivery Device for Use with Anastomosing, Stapling, and Resecting Instruments," now issued as U.S. Pat. No. 6,488,197, each of which is expressly incorporated herein in its entirety by reference thereto.

Figure 2:
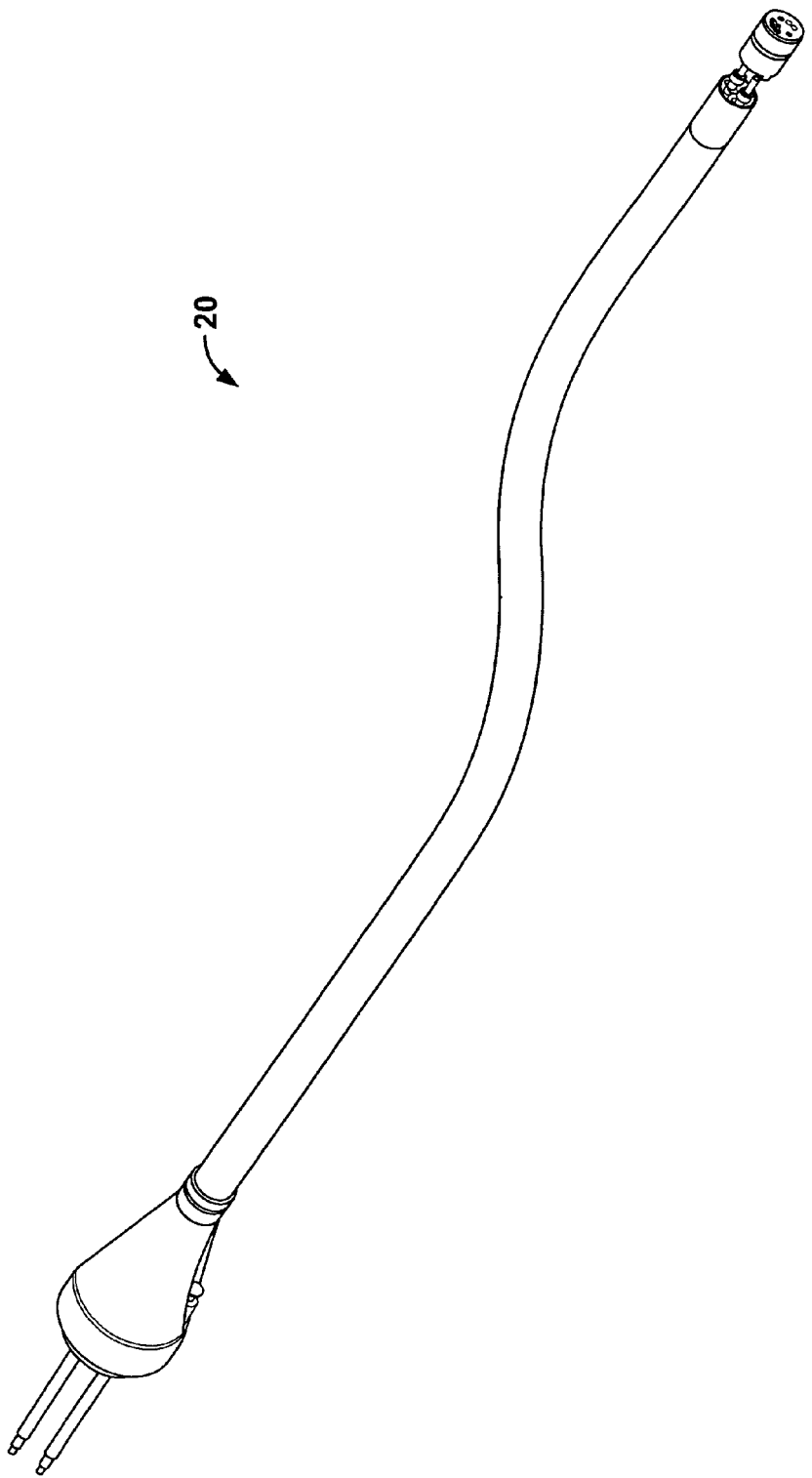
FIG. 2 is a perspective view of the flexible shaft according to an example embodiment of the present invention.

FIG. 2 is a perspective view of the flexible shaft 20. It should be recognized that, while the flexible shaft 20 is illustrated and described herein as being detachably coupled to the remote power console 12, in other example embodiments, the flexible shaft 20 may be permanently coupled to or integral with the remote power console 12. Other aspects and features of the flexible shaft 20 are set forth below in connection with FIGS. 3(a)-15.

Figure 3A:
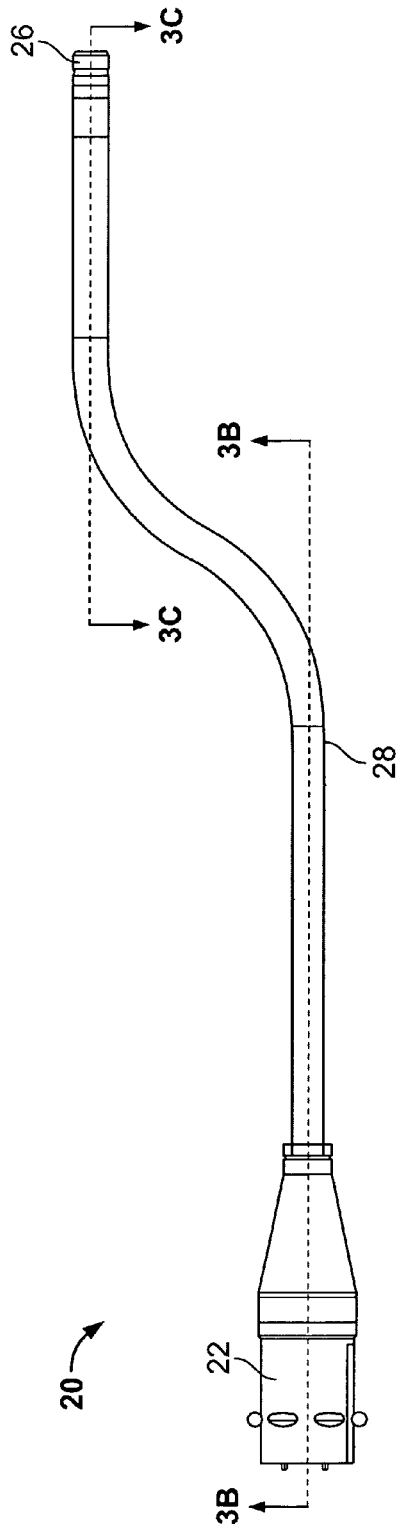
FIG. 3(a) is a side view that illustrates the flexible shaft illustrated in FIG. 2.

FIG. 3(a) is a side view that illustrates the flexible shaft 20. According to an example embodiment, the flexible shaft 20 includes a tubular sheath 28, which may include a coating or other sealing arrangement to provide a fluid-tight seal between an interior channel 40 thereof and the environment. The sheath 28 may be formed of a tissue-compatible, sterilizable elastomeric material. The sheath 28 may also be formed of a material that is autoclavable. The sheath 28 may be formed of a material having a high or relatively high lubricity. For example, the sheath 28 may include Teflon™ (i.e., a fluoropolymer, e.g., polytetrafluoroethylene—"PTFE"), silicone, a Teflon™/silicone combination, such as, for example, SIL-KORE™ (made by W.L. Gore & Associates).

Figure 3B:
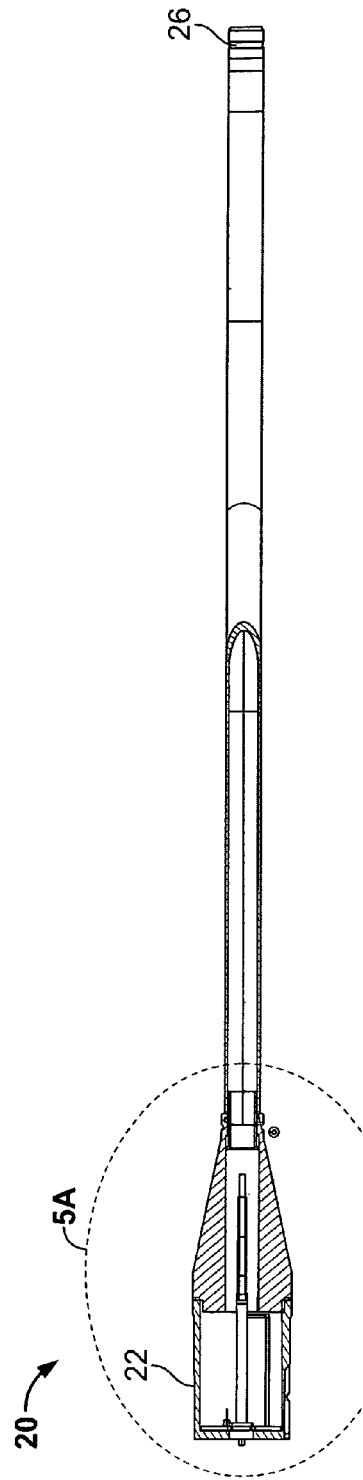
FIG. 3(b) is a bottom view that illustrates, partially in section, the flexible shaft taken along the lines 3B-3B shown in FIG. 3(a).

FIG. 3(b) is a bottom view that illustrates, partially in section, the flexible shaft 20 taken along the lines 3B-3B shown in FIG. 3(a). FIG. 3(b) illustrates in section the proximal end of the flexible shaft 20 and the first coupling 22. Other aspects and features of the first coupling 22 of the flexible shaft 20 are set forth below in connection with FIGS. 5(a), 5(b) and 8.

Figure 3C:
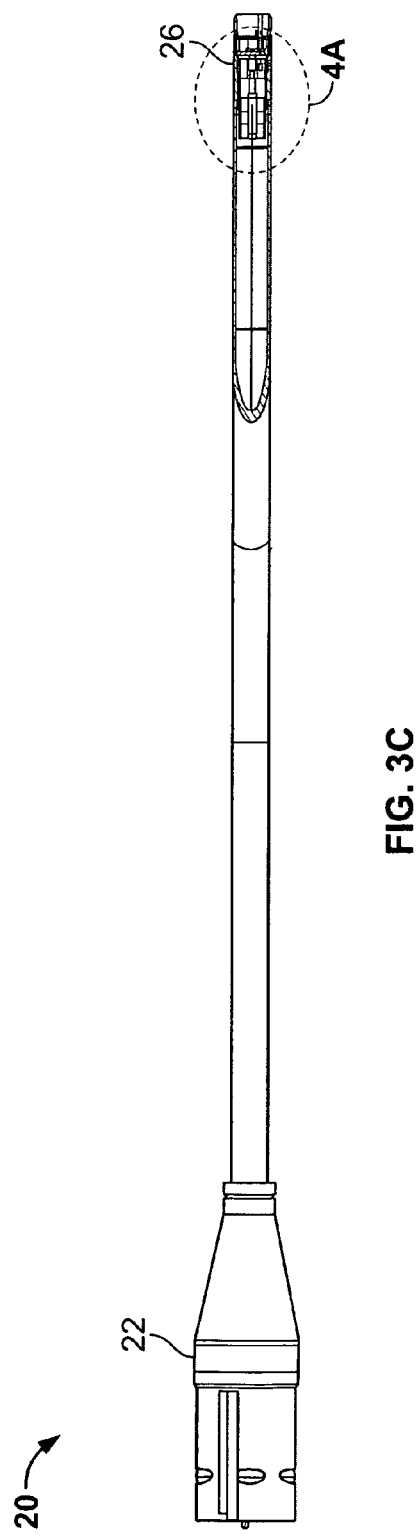
FIG. 3(c) is a top view that illustrates, partially in section, the flexible shaft along the lines 3C-3C shown in FIG. 3(a).

FIG. 3(c) is a top view that illustrates, partially in section, the flexible shaft 20 taken along the lines 3C-3C shown in FIG. 3(a). FIG. 3(c) illustrates in section the distal end of the flexible shaft 20 and the second coupling 26. Other aspects and features of the second coupling 26 of the flexible shaft 20 are set forth below in connection with FIGS. 4(a)-4(h) and 9.

Figure 4A:
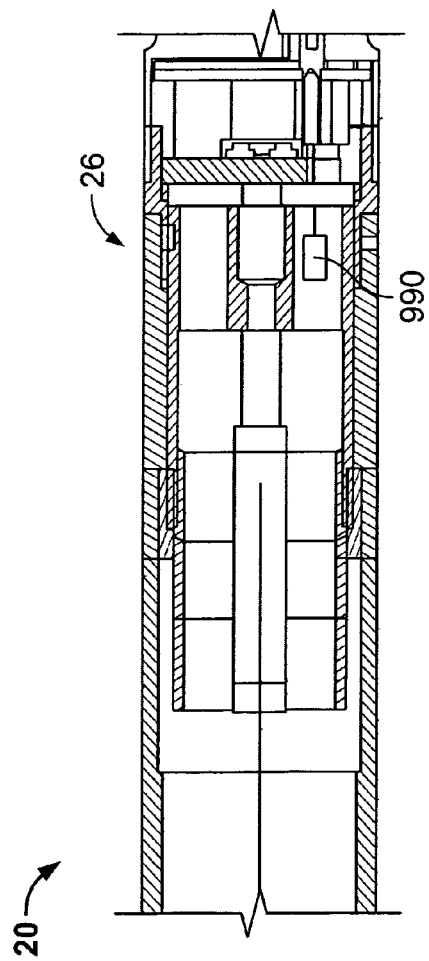
FIG. 4(a) is an enlarged sectional view of a second coupling, as assembled, according to an example embodiment of the present invention.
Figure 4B:
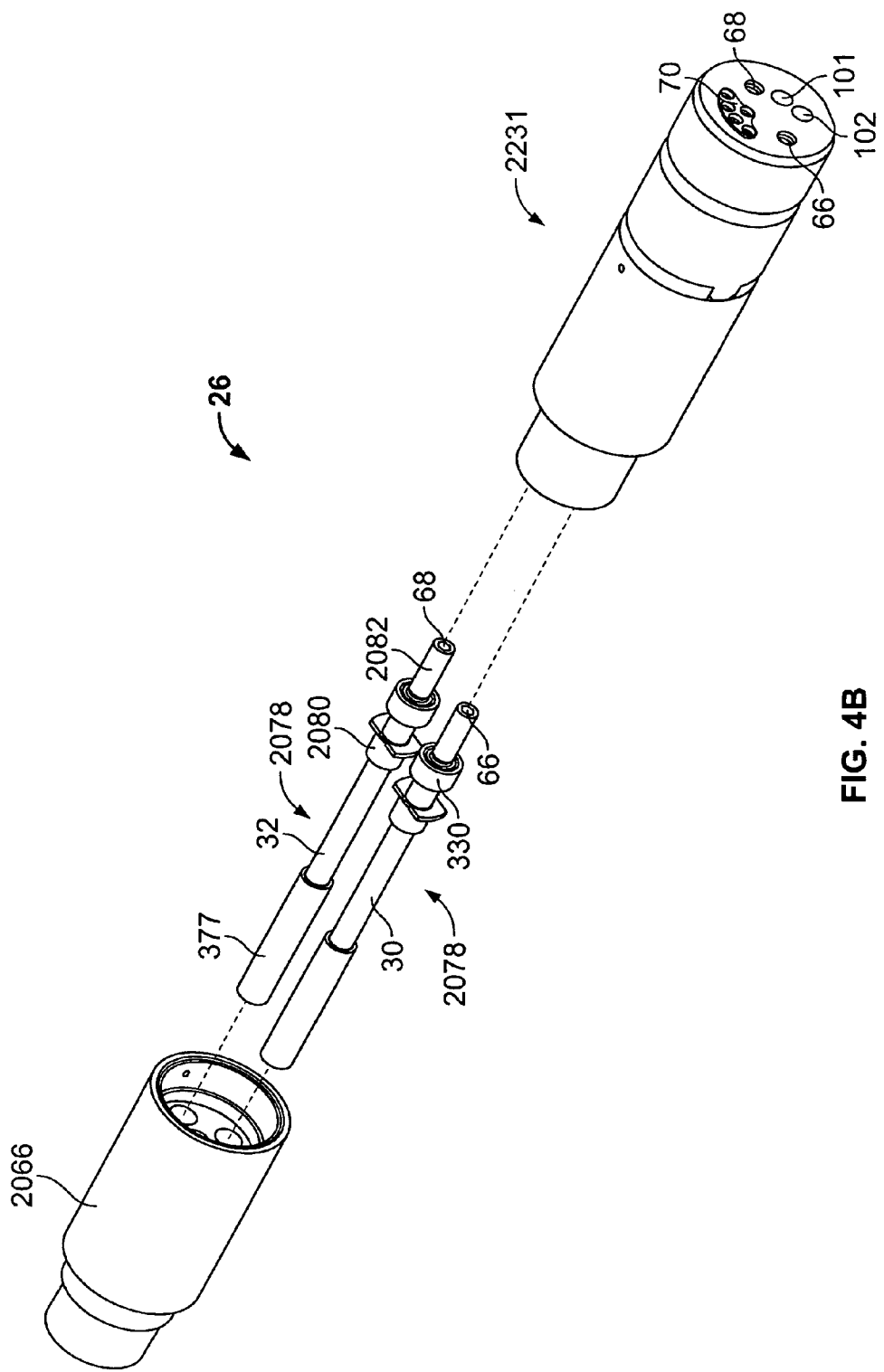
FIG. 4(b) is a front perspective view of the second coupling, according to an example embodiment of the present invention, exploded so as to illustrate some of the components thereof.

FIG. 4(a) is an enlarged sectional view of the second coupling 26, as assembled, according to an example embodiment of the present invention. FIG. 4(b) is a front perspective view of the second coupling 26, according to an example embodiment of the present invention, exploded so as to illustrate some of the components thereof. FIG. 4(b) shows a distal assembly 2231. Disposed within the distal assembly 2231 are first ends of two distal cable end assemblies 2078. Second ends of each one of the distal cable end assemblies 2078 are disposed within respective bores of a distal connector assembly 2066. Referring to each one of the distal cable end assemblies 2078, there is provided a distal cable end 2082. First ends of the distal cable ends 2082 have longitudinally disposed bores that function as connectors 66 and 68, respectively, which are described in greater detail below. The distalmost face of the distal assembly 2231 provides access to the connectors 66, 68 via openings, along with a connector 70 and openings 101b and 102b for providing access to irrigations and aspiration channels 101 and 102, respectively, as discussed further below. Mounted at approximately a midpoint along the outer surface of the distal cable end 2082 is a tip bearing 330. A second end of the distal cable end 2082 engages a distal quadrature ring 2080. Connected to each one of the distal quadrature rings 2080 is a respective drive cable 30, 32 (described in further detail below in connection with FIG. 6), which is surrounded by a sleeve 377, made from, e.g., Teflon™. Each drive cable 30, 32 extends within and along the length of the flexible shaft 20.

Figure 4C:
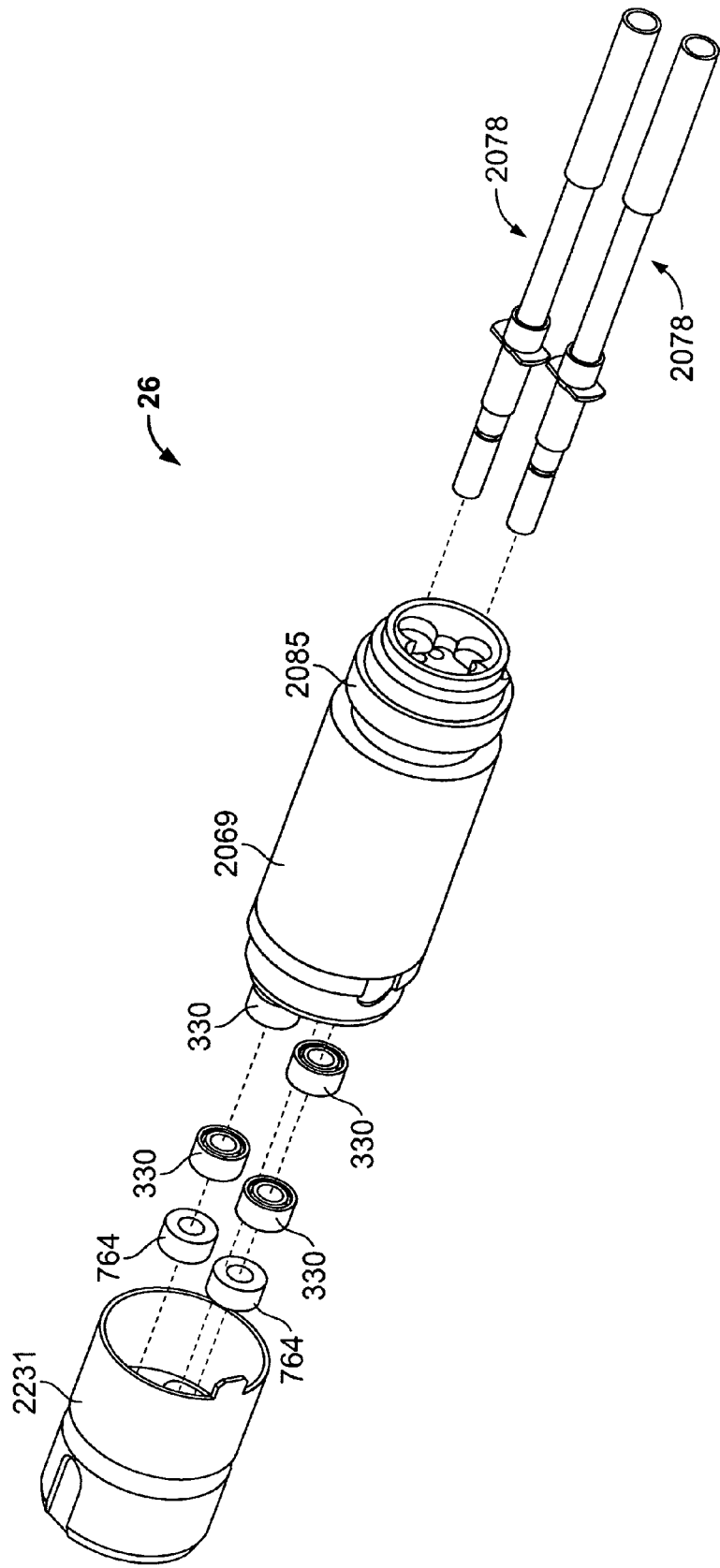
FIG. 4(c) is a rear perspective view of the second coupling shown in FIG. 4(b), partially assembled, showing some additional features thereof.
Figure 4D:
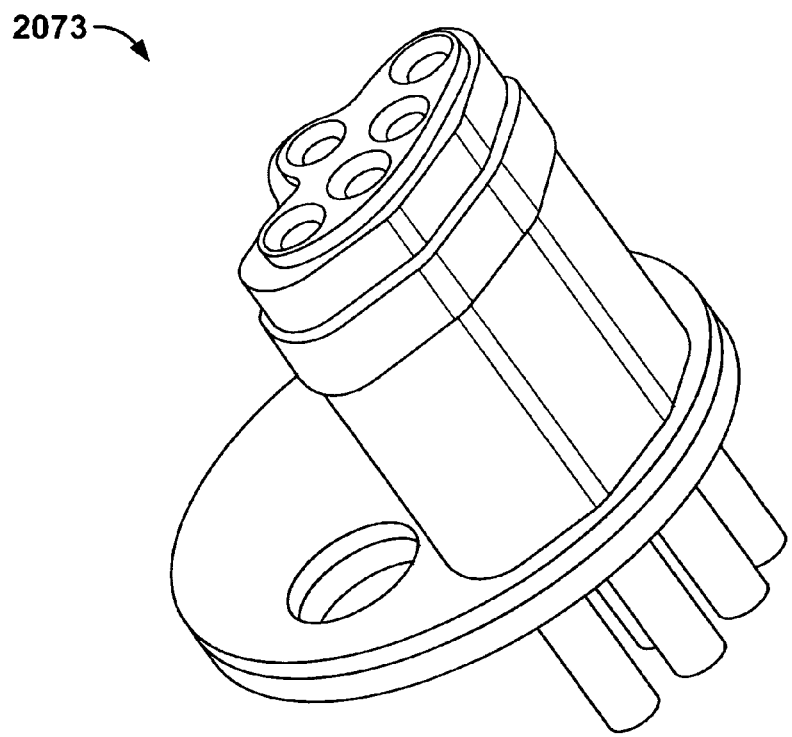
FIGS. 4(d) and 4(e) are front and rear perspective views, respectively, of the distal contact assembly, according to an example embodiment of the present invention, as assembled.
Figure 4E:
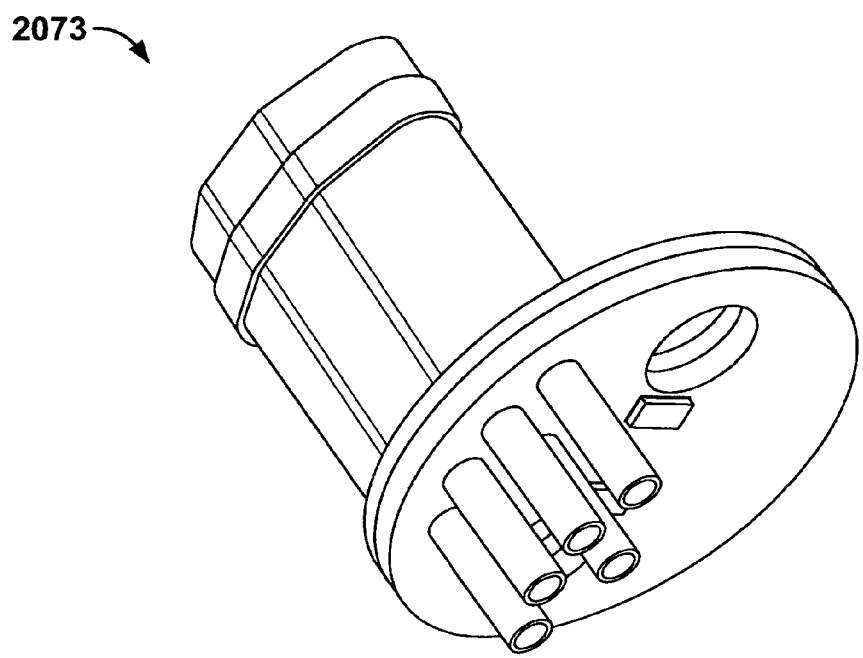
Figure 4F:
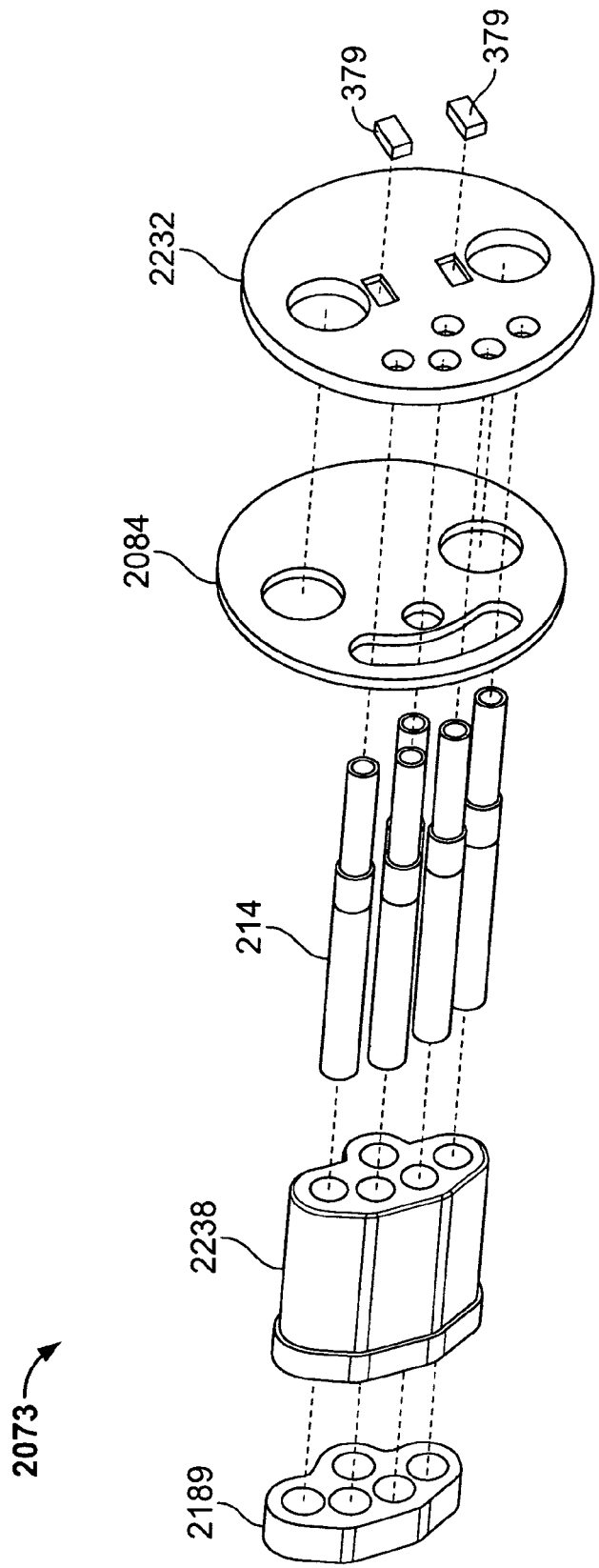
FIG. 4(f) is a rear perspective view of the distal contact assembly, exploded so as to illustrate some of the components thereof.

FIG. 4(c) is a rear perspective view of the second coupling 26 shown in FIG. 4(b), partially assembled, showing some additional features thereof. As shown in FIG. 4(c), the distal cable end assemblies 2078 engage respective bores of a distal optical block 2085. The distal optical block 2085 is connected to a distal press block 2069, in which are disposed the tip bearings 330. Mounted distal relative to the tip bearings 330 are respective seals 764. The distal end of the distal press block 2069 is connected to distal outer case 2237. Mounted within the distal press block 2069 is a distal contact assembly 2073, which is hidden from view in FIG. 4(c) but which is illustrated in FIGS. 4(d) through 4(f). Also mounted within the distal press block 2069 is a distal sensor assembly 2233, which is hidden from view in FIG. 4(c) but which is illustrated in FIG. 4(g).

FIGS. 4(d) and 4(e) are front and rear perspective views, respectively, of the distal contact assembly 2073, according to an example embodiment of the present invention, as assembled. FIG. 4(f) is a rear perspective view of the distal contact assembly 2073, exploded so as to illustrate some of the components thereof. Referring to FIG. 4(f), the distal contact assembly 2073 includes a distal PCB 2232 having a number of bores therethrough. Mounted on the proximal side of the distal PCB 2232 are two light emitting diodes 379. Mounted on the distal side of the distal PCB 2232 is an insulator 2084 having bores that coincide generally with the bores in the distal PCB 2232. Extending through the bores of the insulator 2084 and the distal PCB 2232 are five sockets 214 that are disposed within a contact jacket 2238. The distal end of the contact jacket 2238 is capped by a contact insulator block 2189.

Figure 4G:
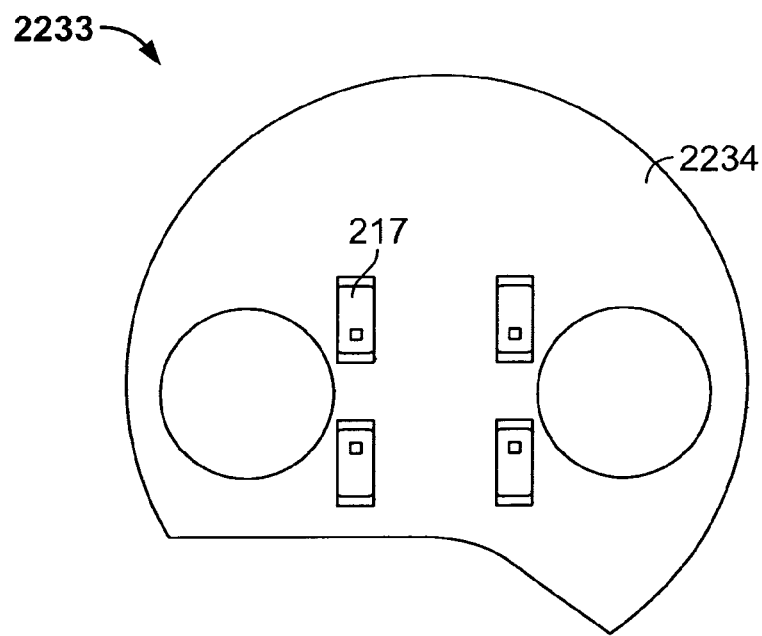
FIG. 4(g) is a frontal view of the distal sensor assembly, according to an example embodiment of the present invention, as assembled.

FIG. 4(g) is a frontal view of the distal sensor assembly 2233, according to an example embodiment of the present invention, as assembled. The distal sensor assembly 2233 includes a distal sensor PCB 2234 having a pair of bores therein. In addition, the distal sensor assembly 2233 has mounted thereon four sensors 217, e.g., phototransistors.

Figure 4H:
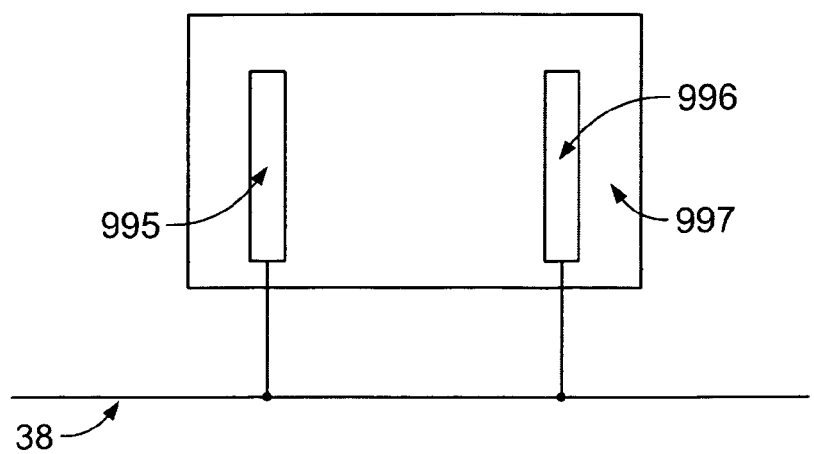
FIG. 4(h) is a schematic representation of a moisture sensor coupled to a data transfer cable.

Referring back to FIG. 4(a), there is shown all of the various components of the second coupling 26 assembled, in section. FIG. 4(a) also illustrates a moisture sensor 990 mounted within the second coupling 26. Additional details of the moisture sensor 990 are shown in FIG. 4(h). Referring to FIG. 4(h), the moisture sensor 990 is coupled to the data transfer cable 38 to communicate an indication of the presence of moisture (e.g., sensed moisture data is communicated) to the remote power console 12. The presence of moisture within the flexible shaft 20 may cause corrosion of the components of the flexible shaft 20, such as, for example, the rotatable drive shafts 30, 32, electronic or electrical components arranged in the flexible shaft 20, etc. In accordance with and/or based on the sensed moisture data, the remote power console 12 may communicate the presence of moisture to a user, such as, for example, by audible or visual signal. The moisture sensor 990 may include a first printed lead 995 and a second printed lead 996, each of which is printed on board element 997 and connected to the data transfer cable 38. The presence of moisture may change the electrical conductivity between the printed leads 995, 996, e.g., the electrical resistance between the printed leads 995, 996 may vary in accordance with the amount of moisture present. It should be appreciated that a moisture sensor 990 may additionally or alternatively be disposed within the elongated sheath of the flexible shaft 20, and coupled to, e.g., data transfer cable 38.

Figure 5A:
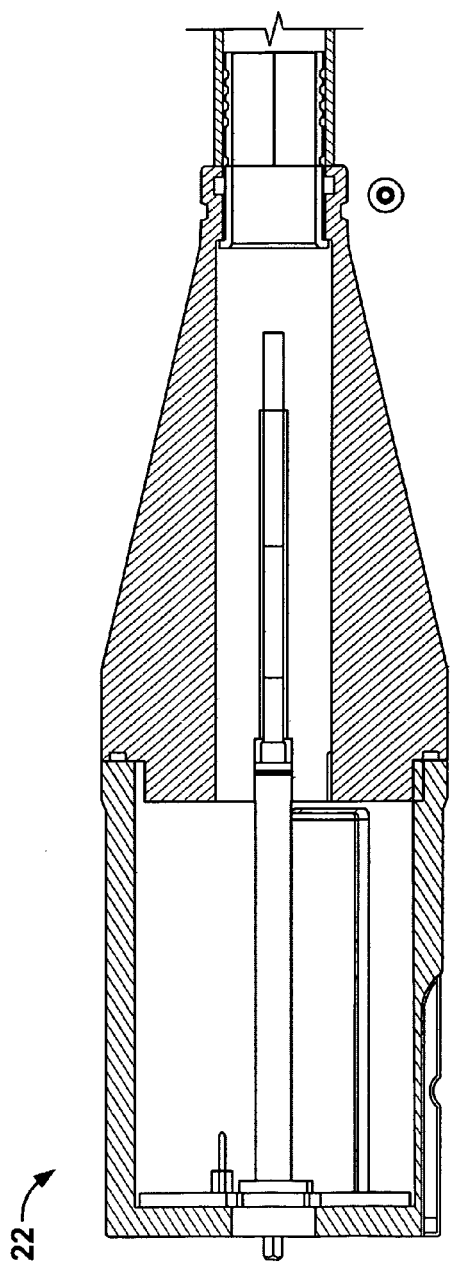
FIG. 5(a) is an enlarged sectional view of the first coupling, as assembled, according to an example embodiment of the present invention.
Figure 5B:
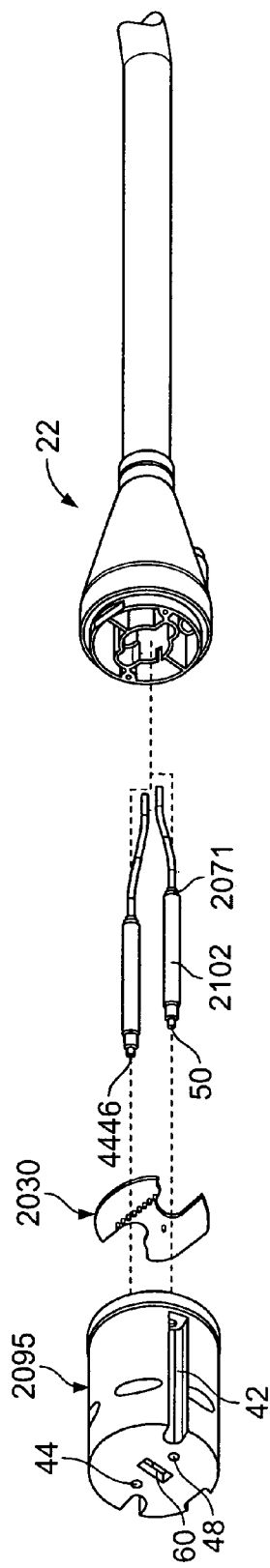
FIG. 5(b) is a front perspective view of the first coupling, according to an example embodiment of the present invention, exploded so as to illustrate some of the components thereof.

FIG. 5(a) is an enlarged sectional view of the first coupling 22, as assembled, according to an example embodiment of the present invention. FIG. 5(b) is a front perspective view of the first coupling 22, according to an embodiment of the present invention, exploded so as to illustrate some of the components thereof. As shown in FIG. 5(b), the first coupling 22 includes a proximal assembly 2095. The proximal assembly 2095 includes a data connector 60. Disposed within the proximal assembly 2095 and mounted to the interior surface at the proximal end of the proximal assembly 2095 is a proximal PCB assembly 2030. Passing through cut-away regions of the proximal PCB assembly 2030 and communicating with bores in the proximal end of the proximal assembly 2095 are proximal drive shafts 2102. The proximal drive shafts 2102 have at their proximal ends non-circular, e.g., hexagonal, drive connectors 44, 48 for engaging respective drive shafts of a motor arrangement within the remote power console 12, as set forth in greater detail below. The distal ends of the proximal drive shafts 2102 engage proximal crimps 2071, that connect the distal ends of the proximal drive shafts 2102, e.g., non-rotatably, to proximal ends of drive cables 30, 32 that extend within the flexible shaft 20. The drive cables 30, 32 connect, e.g., non-rotatably, at their opposite ends to the distal cable end assemblies 2078 located within the first coupling 22, as previously mentioned.

Figure 6:
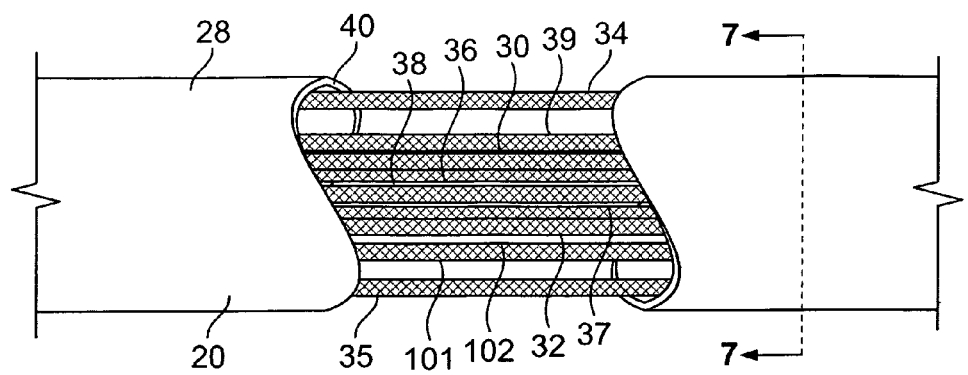
FIG. 6 is a side elevational view, partially in section, of a flexible shaft of the electromechanical surgical device illustrated in FIG. 1.
Figure 7:
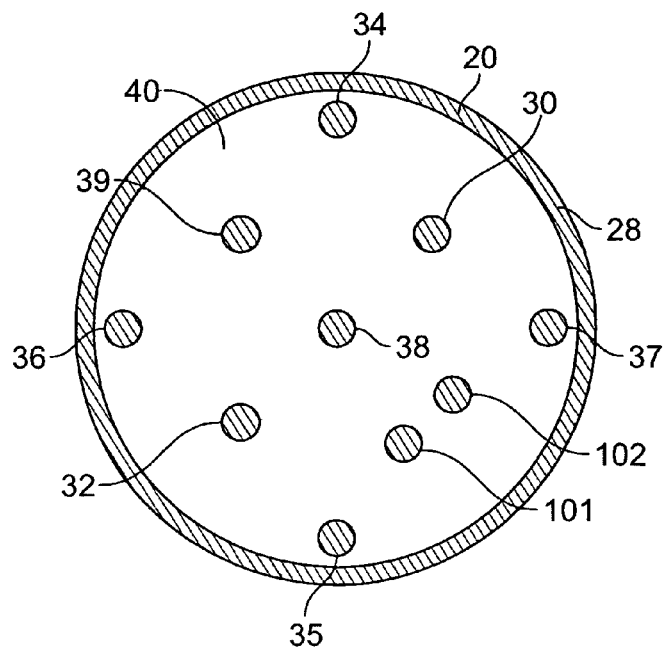
FIG. 7 is a cross-sectional view of the flexible shaft taken along the line 7-7 shown in FIG. 6.

FIG. 6 is a side elevational view, partially in section, of the flexible shaft 20, according to an example embodiment of the present invention. Disposed within the flexible shaft 20, and extending along the entire length thereof, may be a first rotatable drive shaft 30, and a second rotatable drive shaft 32. In addition, according to various example embodiments of the present invention, disposed within the flexible shaft 20 may be steering cables 34, 35, 36 and 37, a data transfer cable 38, a fiber optic cable set 39, irrigation channel 101 and aspiration channel 102. It should be noted that channels, such as 101, 102 may be used for other purposes other than irrigating and/or aspirating a surgical site, e.g., they may be employed for passing a surgical instrument therethrough. Furthermore, it should be noted that, while the fiber optic cable set 39 is illustrated as being a single bundle of fiber optic cables, in other exemplary embodiments, the fiber optic cables may be separately arranged. Any number of fiber optic cables may be employed, as set forth below. FIG. 7 is a cross-sectional view of the flexible shaft 20 taken along the line 7-7 shown in FIG. 6 and further illustrates the several cables 30, 32, 34-39 and channels 101, 102. Each of the several cables 30, 32, 34-39 may be contained within a respective sheath.

The first rotatable drive shaft 30 and the second rotatable drive shaft 32 may be configured, for example, as highly flexible drive shafts, such as, for example, braided or helical drive cables. It should be understood that such highly flexible drive cables may have limited torque transmission characteristics and capabilities. It should also be understood that surgical instruments, such as surgical stapler attachment or the like, or other attachments detachably attachable to the flexible shaft 20 may require a higher torque input than the torque transmittable by the drive shafts 30, 32. The drive shafts 30, 32 may thus be configured to transmit low torque but high speed, the high speed/low torque being converted to low speed/high torque by gearing arrangements disposed, for example, at the distal end and/or the proximal end of the flexible shaft 20, in the surgical instrument or attachment and/or in the remote power console 12. It should be appreciated that such gearing arrangement(s) may be provided at any suitable location along the power train between the motors disposed in the housing 14 and the attached surgical instrument or other attachment detachably attachable to the flexible shaft 20. Such gearing arrangement(s) may be provided in the surgical instrument or other attachment detachably attachable to the flexible shaft 20. Such gearing arrangement(s) may include, for example, a spur gear arrangement, a planetary gear arrangement, a harmonic gear arrangement, cycloidal drive arrangement, an epicyclic gear arrangement, etc.

Figure 8:
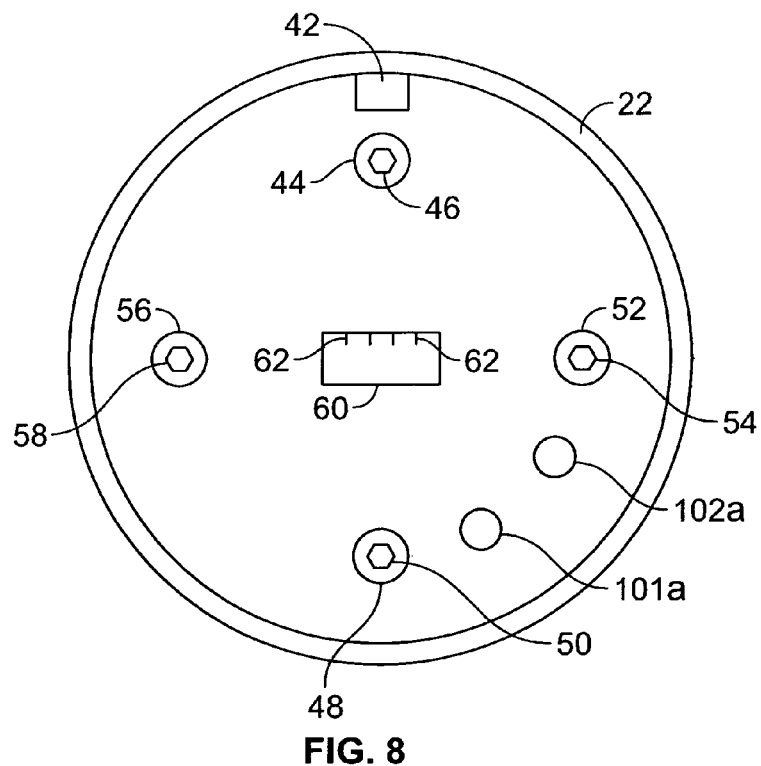
FIG. 8 is a rear end view of a first coupling of the flexible shaft illustrated in FIG. 2.

Referring now to FIG. 8, there is seen a schematic representation of a rear end view of the first coupling 22. The first coupling 22 includes a first connector 44 and a second connector 48, each rotatably arranged with respect to the first coupling 22. Each of the connectors 44, 48, includes a respective projection 46, 50 that may extend through the proximal-most face of the first coupling 22. As shown in FIG. 8, each projection 46, 50 may be hexagonally shaped. It should be appreciated, however, that the projections 46, 50 may have any shape and configuration to non-rotatably couple and rigidly attach the connectors 44, 48 to respective drive shafts of the motor arrangement contained within the housing 12, as more fully described below. It should be appreciated that complementary recesses may be provided on respective drive shafts of the motor arrangement to thereby drive the drive elements of the flexible shaft 20 as described below. It should also be appreciated that the projection may be provided on the drive shafts and complementary recesses may be provided on the connectors 44, 48. Any other coupling arrangement configured to non-rotatably and releasably couple the connectors 44, 48 and the drive shafts of the motor arrangement may be provided.

One of the connectors 44, 48 is non-rotatably secured to the first drive shaft 30, and another one of the connectors 44, 48 is non-rotatably secured to the second drive shaft 32. The remaining two of the connectors 44, 48, 52, 56 engage with transmission elements configured to apply tensile forces on the steering cables 34, 35, 36, 37 to thereby steer the distal end 24 of the flexible shaft 20. The first coupling 22 may include the openings 101a, 102a connected to the irrigation and aspiration channels 101, 102, respectively, for introducing and/or removing fluids from the surgical site.

The data transfer cable 38 is electrically and logically connected with the data connector 60. The data connector 60 includes, for example, electrical contacts 62, corresponding to and equal in number to the number of individual wires contained in the data cable 38. The first coupling 22 includes a key structure 42 to properly orient the first coupling 22 to a mating and complementary coupling arrangement disposed on the housing 12. Such key structure 42 may be provided on either one, or both, of the first coupling 22 and the mating and complementary coupling arrangement disposed on the housing 12. The first coupling 22 may include a quick-connect type connector, which may use, for example, a simple pushing motion to engage the first coupling 22 to the housing 12. Seals may be provided in conjunction with any of the several connectors 44, 48, 60 to provide a fluid-tight seal between the interior of the first coupling 22 and the environment.

Figure 9:
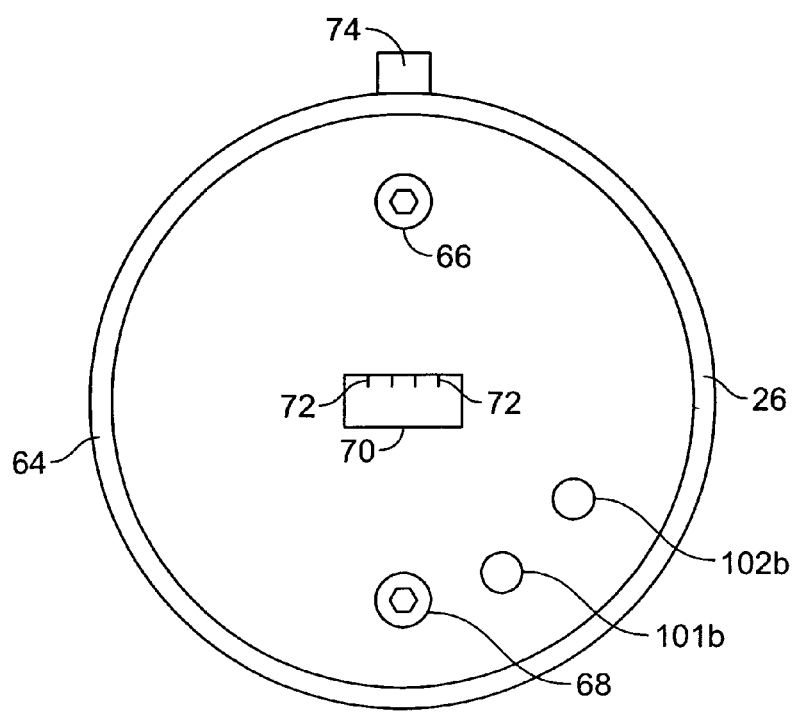
FIG. 9 is a front end view of a second coupling of the flexible shaft illustrated in FIG. 2.

Referring now to FIG. 9, there is seen a schematic representation of a front end view of the second coupling 26 of the flexible shaft 20. The second coupling 26 includes a first connector 66 and a second connector 68, each being rotatably arranged with respect to the second coupling 26 and each being non-rotatably secured to a distal end of a respective one of the first and second drive shafts 30, 32. A quick-connect type fitting 64 may be provided on the second coupling 26 for detachably securing the surgical instrument or attachment thereto. The quick-connect type fitting 64 may be, for example, a rotary quick-connect type fitting, a bayonet type fitting, etc. A key structure 74 may be provided on the second coupling 26 for properly aligning the surgical instrument or attachment to the second coupling 26. The key structure 74 or other arrangement for properly aligning the surgical instrument or attachment to the flexible shaft 20 may be provided on either one, or both, of the second coupling 26 and the surgical instrument or attachment. In addition, the quick-connect type fitting may be provided on the surgical instrument or attachment. A data connector 70, having electrical contacts 72, is also provided in the second coupling 26. Like the data connector 60 of the first coupling 22, the data connector 70 of the second coupling 26 includes the contacts 72 electrically and logically connected to the respective wires of the data transfer cable 38 and the contacts 62 of the data connector 60. Seals may be provided in conjunction with the connectors 66, 68, 70 to provide a fluid-tight seal between the interior of the second coupling 26 and the environment. The second coupling 26 may include the openings 101b, 102b connected to the irrigation and aspiration channels 101, 102, respectively, for introducing and/or removing fluids from the surgical site.

Disposed within housing 14 of the remote power console 12 are electromechanical driver elements configured to drive the drive shafts 30, 32 to thereby operate the electromechanical surgical device 10 and the surgical instrument or attachment attached to the second coupling 26. In the example embodiment illustrated schematically in FIG. 10, five electric motors 76, 80, 84, 90, 96, each operating via a power source, may be disposed in the remote power console 12. It should be appreciated, however, that any appropriate number of motors may be provided, and the motors may operate via battery power, line current, a DC power supply, an electronically controlled DC power supply, etc. It should also be appreciated that the motors may be connected to a DC power supply, which is in turn connected to line current and which supplies the operating current to the motors.

Figure 10:
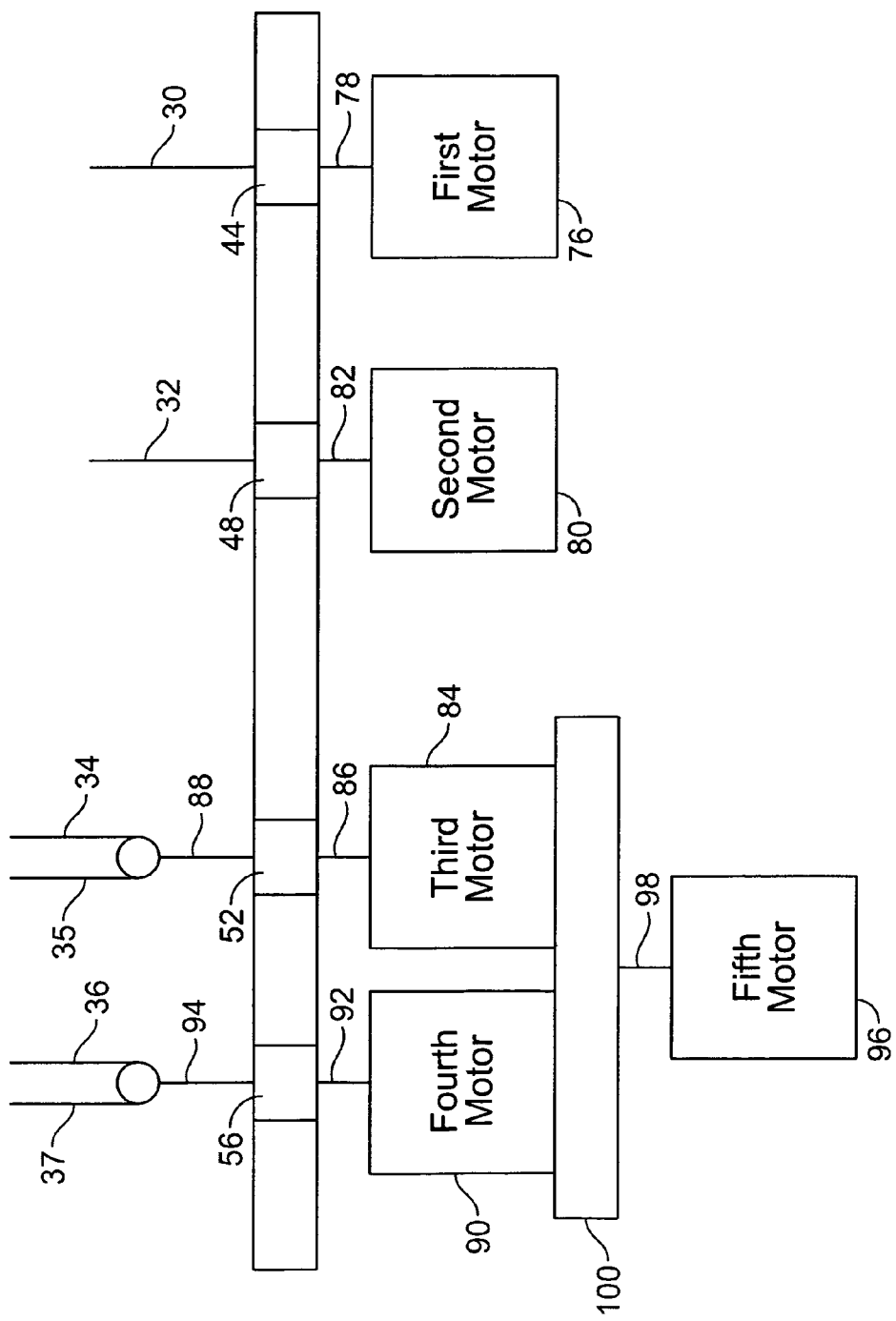
FIG. 10 is a schematic view illustrating a motor arrangement of the electromechanical surgical device illustrated in FIG. 1.

FIG. 10 illustrates schematically one possible arrangement of motors. An output shaft 78 of a first motor 76 engages with the first connector 44 of the first coupling 22 when the first coupling 22, and, therefore, the flexible shaft 20, is engaged with the housing 14 to thereby drive the first drive shaft 30 and the first connector 66 of the second coupling 26. Similarly, an output shaft 82 of a second motor 80 engages the second connector 48 of the first coupling 22 when the first coupling 22, and, therefore, the flexible shaft 20 is engaged with the housing 14 to thereby drive the second drive shaft 32 and the second connector 68 of second coupling 26.

As set forth above, the flexible shaft 20 may include steering cables, such as steering cables 34, 35, 36 and 37 that may be employed to steer the flexible shaft 20. FIG. 10 also illustrates a motor arrangement that may be employed to utilize such steering cables in those example embodiments of the flexible shaft 20 that include same. For example, FIG. 10 illustrates that an output shaft 86 of a third motor 84 engages the third connector 52 of the first coupling 22 when the first coupling 22, and, therefore, the flexible shaft 20, is engaged with the housing 14 to thereby drive the first and second steering cables 34, 35 via a first pulley arrangement 88. An output shaft 92 of a fourth motor 90 engages the fourth connector 56 of the first coupling 22 when the first coupling 22, and, therefore, the flexible shaft 20, is engaged with the housing 14 to thereby drive the third and fourth steering cables 36, 37 via a second pulley arrangement 94. The third and fourth motors 84, 90 may be secured on a carriage 100, which is selectively movable via an output shaft 98 of a fifth motor 96 between a first position and a second position to selectively engage and disengage the third and fourth motors 84, 90 with the respective pulley arrangement 88, 94 to thereby permit the flexible shaft 20 to become taut and steerable or limp as necessary. It should be appreciated that other mechanical, electrical or electro-mechanical mechanisms may be used to selectively engage and disengage the steering mechanism. The motors may be arranged and configured as described, for example, in U.S. patent application Ser. No. 09/510,923, entitled "A Carriage Assembly for Controlling a Steering Wire Mechanism Within a Flexible Shaft," now issued as U.S. Pat. No. 6,517,565, which is expressly incorporated herein in its entirety by reference thereto.

It should be appreciated, that any one or more of the motors 76, 80, 84, 90, 96 may be high-speed/low-torque motors or low-speed/high-torque motors. As indicated above, the first rotatable drive shaft 30 and the second rotatable drive shaft 32 may be configured to transmit high speed and low torque. Thus, the first motor 76 and the second motor 80 may be configured as high-speed/low-torque motors. Alternatively, the first motor 76 and the second motor 80 may be configured as low-speed/high-torque motors with a torque-reducing/speed-increasing gear arrangement disposed between the first motor 76 and the second motor 80 and a respective one of the first rotatable drive shaft 30 and the second rotatable drive shaft 32. Such torque-reducing/speed-increasing gear arrangement may include, for example, a spur gear arrangement, a planetary gear arrangement, a harmonic gear arrangement, cycloidal drive arrangement, an epicyclic gear arrangement, etc. It should be appreciated that any such gear arrangement may be disposed within the remote power console 12 or in the proximal end of the flexible shaft 20, such as, for example, in the first coupling 22. It should be appreciated that the gear arrangement(s) are provided at the distal and/or proximal ends of the first rotatable drive shaft 30 and/or the second rotatable drive shaft 32 to prevent windup and breakage thereof.

Figure 11:
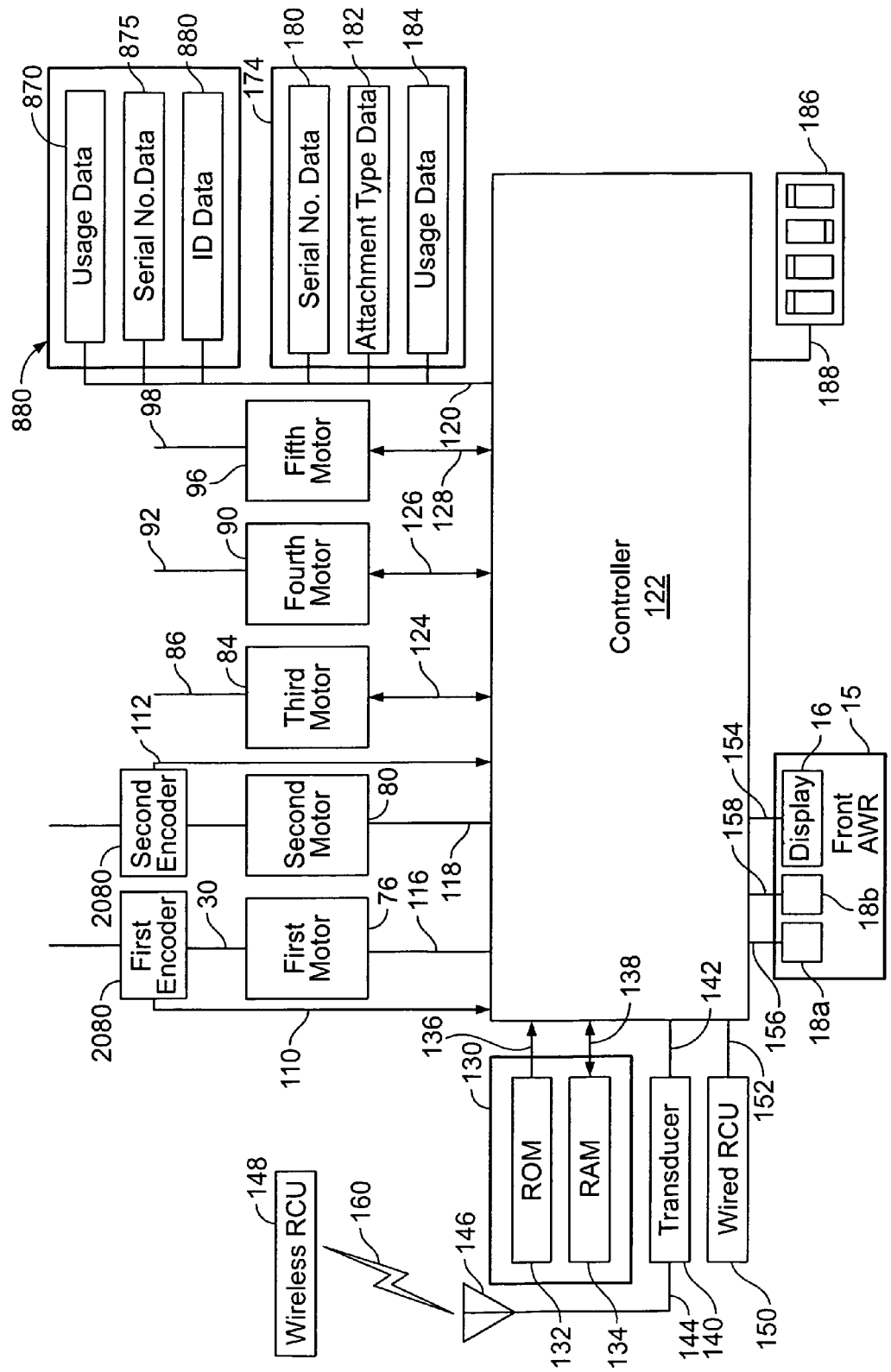
FIG. 11 is a schematic view of the electromechanical surgical device illustrated in FIG. 1.

Referring now to FIG. 11, there is seen a schematic view of the electromechanical surgical device 10. A controller 122 is provided in the housing 14 of remote power console 12 and is configured to control all functions and operations of the electromechanical surgical device 10 and any surgical instrument or attachment attached to the flexible shaft 20. A memory unit 130 is provided and may include memory devices, such as, a ROM component 132 and/or a RAM component 134. The ROM component 132 is in electrical and logical communication with the controller 122 via a line 136, and the RAM component 134 is in electrical and logical communication with the controller 122 via a line 138. The RAM component 134 may include any type of random-access memory, such as, for example, a magnetic memory device, an optical memory device, a magneto-optical memory device, an electronic memory device, etc. Similarly, the ROM component 132 may include any type of read-only memory, such as, for example, a removable memory device, such as a PC-Card or PCMCIA-type device. It should be appreciated that the ROM component 132 and the RAM component 134 may be arranged as a single unit or may be separate units and that the ROM component 132 and/or the RAM component 134 may be provided in the form of a PC-Card or PCMCIA-type device. The controller 122 is further connected to the front panel 15 of the housing 14 and, more particularly, to the display device 16 via a line 154 and the indicators 18a, 18b via respective lines 156, 158. The lines 116, 118, 124, 126, 128 electrically and logically connect the controller 122 to the first, second, third, fourth and fifth motors 76, 80, 84, 90, 96, respectively. A wired remote control unit ("RCU") 150 is electrically and logically connected to the controller 122 via a line 152. A wireless RCU 148 is also provided and communicates via a wireless link 160 with a receiving/sending unit 146 connected via the line 144 to a transceiver 140. The transceiver 140 is electrically and logically connected to the controller 122 via a line 142. The wireless link 160 may be, for example, an optical link, such as an infrared link, a radio link or any other form of wireless communication link.

A switch device 186, which may be, for example, an array of DIP switches, may be connected to the controller 122 via a line 188. The switch device 186 may be used, for example, to select one of a plurality of languages used in displaying messages and prompts on the display device 16. The messages and prompts may relate to, for example, the operation and/or the status of the electromechanical surgical device 10 and/or to any surgical instrument or attachment attached thereto.

According to the example embodiment of the present invention, each one of the quadrature rings 2080 is provided within the second coupling 26 and is configured to output a signal in response to and in accordance with the rotation of a respective one of the first and second drive shafts 30, 32. The signal output by each of the quadrature rings 2080 may represent the rotational position of the respective drive shaft 30, 32 as well as the rotational direction thereof. Although the quadrature rings 2080 are described as being disposed within the second coupling 26, it should be appreciated that the quadrature rings 2080 may be provided at any location between the motor system and the surgical instrument or attachment. It should be appreciated that providing the quadrature rings 2080 within the second coupling 26 or at the distal end of the flexible shaft 20 provides for an accurate determination of the drive shaft rotation. If the quadrature rings 2080 are disposed at the proximal end of the flexible shaft 20, windup of the first and second rotatable drive shafts 30, 32 may result in measurement error.

Figure 12:
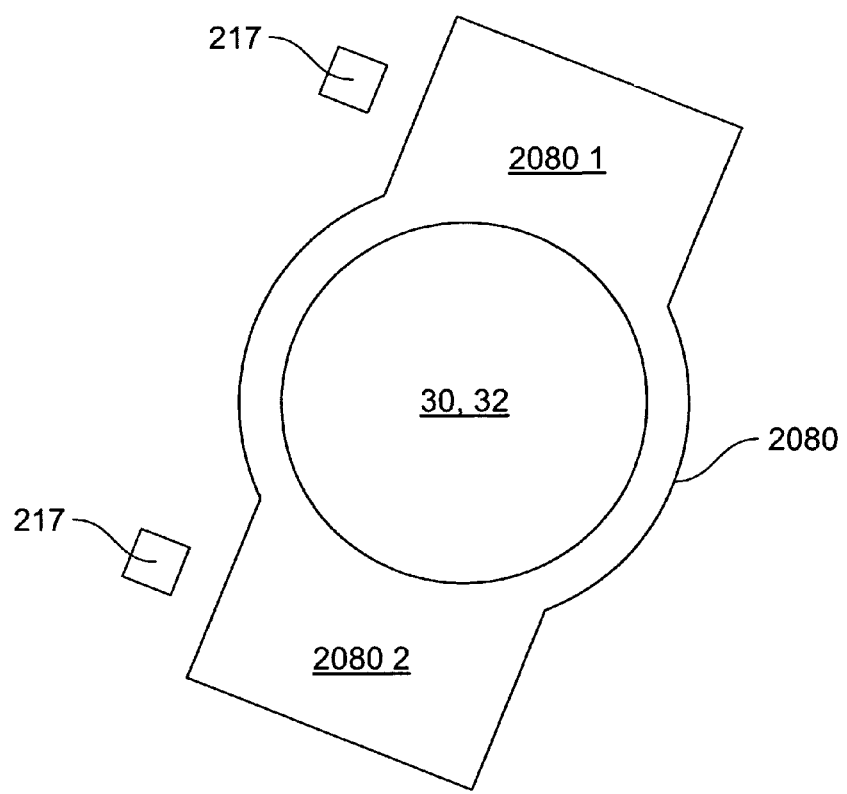
FIG. 12 is a schematic view of a quadrature ring arrangement of the flexible shaft illustrated in FIG. 4(b).

FIG. 12 is a schematic view of a quadrature ring 2080 arrangement. Mounted non-rotatably on one of the drive shafts 30, 32 is the quadrature ring 2080 having a first tab 20801 and a second tab 20802. The quadrature ring 2080 arrangement further includes the first and second light sources 217, e.g., light-emitting diodes, phototransistor, etc., which are disposed approximately 90° apart relative to the longitudinal, or rotational, axis of drive shaft 30, 32. In addition, the quadrature ring 2080 arrangements may include the fiber optic cable set 39, e.g., for transmitting light along the length of the flexible shaft 20 between the light sources 217 and the remote power console 12. The first and second tabs 20801 and 20802 of the quadrature rings 2080 are configured to alternately block and allow light emitted from the light sources 217 to reach the remote power console 217 via the fiber optic cables. It should be appreciated that, while the quadrature ring 2080 is described and shown herein as being a separate structure that is mounted onto respective rotatable drive shafts 30, 32, any member that rotate along with the rotatable drive shafts 30, 32 and that perform the functions of separate quadrature rings 2080 may be employed, e.g., the rotatable drive shafts 30, 32 themselves may instead have integral structures, e.g., tabs. Based on the receipt by the remote power console 12 of the light emitted from the respective light sources 217, the angular position of the drive shaft 30, 32 may be determined within one-quarter revolution and the direction of rotation of the drive shaft 30, 32 may be determined. The output of each quadrature ring 2080 is transmitted to the controller 122. The controller 122, by tracking the angular position and rotational direction of the drive shafts 30, 32 based on the output signal from the quadrature rings 2080, can thereby determine the position and/or state of the components of the surgical instrument or attachment connected to the electromechanical surgical device 10. That is, by counting the revolutions of the drive shaft 30, 32, the controller 122 can determine the position and/or state of the components of the surgical instrument or attachment connected to the electromechanical surgical device 10. It should be appreciated that any number of tabs may be provided depending on the desired resolution of angular movement.

For example, the second coupling 26 of the flexible shaft 20 may detachably attach to a surgical stapler attachment thereto, the surgical stapler attachment including an anvil stem that is extended and retracted to clamp a section of tissue against an anvil, and further including a staple driver/cutter that cuts the section of tissue and drives a set of staples against the anvil for stapling the section of tissue. The extension and retraction of the anvil may be effected by the operation of the first motor 76, and the extension and retraction of the staple driver/cutter may be effected by the operation of the second motor 80. The pitch of a drive shaft for driving the anvil and the pitch of the drive shaft for driving the stapler driver/cutter drive shaft may be predetermined and known quantities, such that the advancement distance of the anvil and of the staple driver/cutter may be functions of, and ascertainable on the basis of, the rotation of the respective drive shaft 30, 32. By ascertaining an absolute position of the anvil and the staple driver/cutter at a point in time, the relative displacement of the anvil and staple driver/cutter, based on the output signal from the respective quadrature rings 2080 and the known pitches of the anvil drive shaft and staple driver/cutter drive shaft, may be used to ascertain the absolute position of the anvil and staple driver/cutter at all times thereafter. The absolute position of the anvil and staple driver/cutter may be fixed and ascertained at the time that the circular surgical stapler attachment is first coupled to the flexible shaft 20. Alternatively, the position of the anvil and the staple driver/cutter relative to, for example, a separate component of the surgical stapler attachment may be determined based on the output signal from the quadrature rings 2080.

Figure 13:
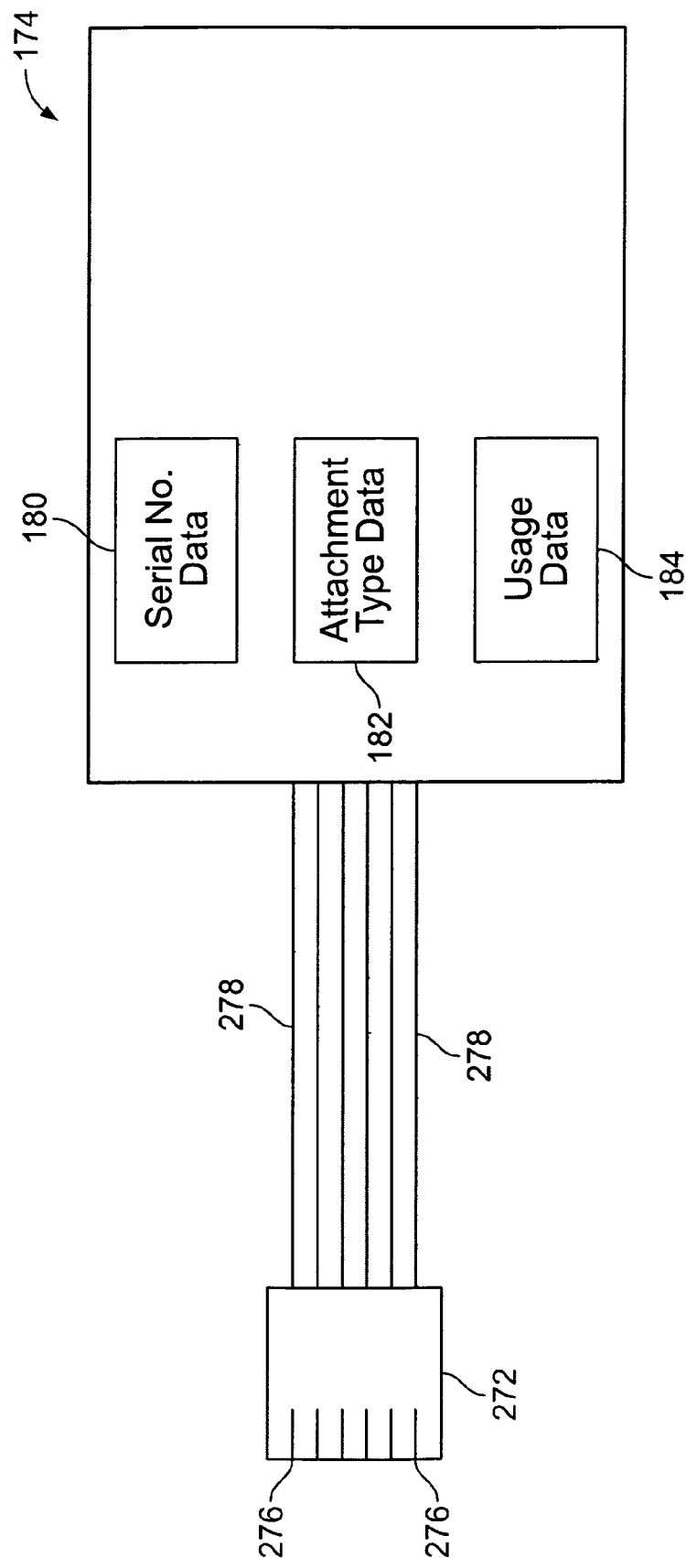
FIG. 13 is a schematic view of a memory device of a surgical attachment and/or the flexible shaft.

Referring again to FIG. 11, the surgical stapler attachment and the flexible shaft 20 may include memory units 174, 850, respectively, electrically and logically connected via data cables within the flexible shaft 20 to the controller 122. The memory units 174, 850 may be in the form of, for example, an EEPROM, EPROM, etc. FIG. 13 schematically illustrates the memory unit 174, according to an example embodiment of the present invention. The memory unit 850 may have a similar arrangement as shown in FIG. 13. As seen in FIG. 13, a data connector 272 includes contacts 276, each electrically and logically connected to the memory unit 174 via a respective line 278. The memory unit 174 is configured to store, for example, a serial number data 180, an attachment type identifier (ID) data 182 and a usage data 184. The memory unit 174 may additionally store other data. Both the serial number data 180 and the ID data 182 may be configured as read-only data. In the example embodiment, the serial number data 180 is data uniquely identifying the particular surgical instrument or attachment, whereas the ID data 182 is data identifying the type of the attachment, such as, for example, a circular surgical stapler attachment, a linear surgical stapler attachment, etc. The usage data 184 represents usage of the particular attachment, such as, for example, the number of times an anvil of a surgical stapler attachment connected via the flexible shaft 20 has been advanced or the number of times that the staple driver/cutter of the circular surgical stapler attachment has been advanced or fired.

It should be appreciated that each type of surgical instrument or attachment attachable to the distal end 24 of the flexible shaft 20 may be designed and configured to be used a single time or multiple times. The surgical instrument or attachment may also be designed and configured to be used a predetermined number of times. Accordingly, the usage data 184 may be used to determine whether the surgical instrument or attachment has been used and whether the number of uses has exceeded the maximum number of permitted uses. As more fully described below, an attempt to use a surgical instrument or attachment after the maximum number of permitted uses has been reached will generate an ERROR condition.

It should be appreciated that the discussion hereinabove of any particular surgical attachment, e.g., a circular surgical stapler attachment, is intended to be merely an example of a surgical attachment that may be used in conjunction with the flexible shaft 20. It should be further appreciated that any other type of surgical instrument or attachment, such as those enumerated hereinabove, may be used in conjunction with the flexible shaft 20. Regardless of the particular type of surgical instrument or attachment, in the example embodiment of the present invention, the surgical instrument or attachment may include a coupling element, as may be necessary for proper operation of the surgical instrument or attachment, as well as the memory unit 174. Although the drive shafts and motors are described herein as effecting particular functions of a circular surgical stapler attachment, it should be appreciated that the drive shafts and motors may effect the same or other functions of other types of surgical instruments or attachments.

Referring again to FIG. 11, in accordance with the example embodiment of the present invention, the controller 122 is configured to read the ID data 182 from the memory unit 174 of the surgical instrument or attachment when the surgical instrument or attachment is initially connected to the flexible shaft 20, and the controller 122 is configured to read the ID data 880 from the memory unit 850 of the flexible shaft 20. The memory units 174, 850 may be electrically and logically connected in parallel to the controller 122 via line 120 of data transfer cable 38 or, alternatively, may be connected to the controller 122 via respective dedicated lines.

Based on the read usage data 870 of the flexible shaft 20, the controller 122 may prevent the surgical device 10 from driving the flexible shaft 20. As described above, a particular flexible shaft 20 may be designed and configured to be used a single time, multiple times, or a predetermined number of times. Accordingly, the usage data 870 may be read by the controller 122 to determine whether the flexible shaft 20 has been used and whether the number of uses has exceeded a maximum number of permitted uses. If the maximum number of uses has been exceeded, the controller 122 may prevent subsequent attempts to use the flexible shaft 20.

Additionally, the controller 122 may write the usage data 870 to the memory unit 850 of the flexible shaft 20. The written usage data 870 may include information relating to, for example, a number of revolutions of one or both rotatable drive shafts 30, 32, a number of uses of one or both rotatable drive shafts 30, 32, a number of firings of one or both rotatable drive shafts 30, 32, and/or the number of times the flexible shaft 20 has been used, etc. It should be appreciated that the written usage data 870 may include information in any form suitable to indicate a change in any condition of the flexible shaft 20 that may relate, for example, to usage.

Based on the read ID data 182, the controller 122 is configured to read or select from the memory unit 130, an operating program or algorithm corresponding to the type of surgical instrument or attachment connected to the flexible shaft 20. The memory unit 130 is configured to store the operating programs or algorithms for each available type of surgical instrument or attachment, the controller 122 selecting and/or reading the operating program or algorithm from the memory unit 130 in accordance with the ID data 182 read from the memory unit 174 of an attached surgical instrument or attachment. As indicated above, the memory unit 130 may include a removable ROM component 132 and/or RAM component 134. Thus, the operating programs or algorithms stored in the memory unit 130 may be updated, added, deleted, improved or otherwise revised as necessary. The operating programs or algorithms stored in the memory unit 130 may be customizable based on, for example, specialized needs of the user. A data entry device, such as, for example, a keyboard, a mouse, a pointing device, a touch screen, etc., may be connected to the memory unit 130 via, for example, a data connector port, to facilitate the customization of the operating programs or algorithms. Alternatively or additionally, the operating programs or algorithms may be customized and preprogrammed into the memory unit 130 remotely from the electro-mechanical surgical device 10. It should be appreciated that the serial number data 180 and/or usage data 184 may also be used to determine which of a plurality of operating programs or algorithms is read or selected from the memory unit 130. It should be appreciated that the operating program or algorithm may alternatively be stored in the memory unit 174 of the surgical instrument or attachment and transferred to the controller 122 via the data transfer cable 38. Once the appropriate operating program or algorithm is read or selected by, or transmitted to, the controller 122, the controller 122 causes the operating program or algorithm to be executed in accordance with operations performed by the user via the wired RCU 150 and/or the wireless RCU 148. As indicated hereinabove, the controller 122 is electrically and logically connected with the first, second, third, fourth and fifth motors 76, 80, 84, 90, 96 via respective lines 116, 118, 124, 126, 128 and controls such motors 76, 80, 84, 90, 96 in accordance with the read, selected or transmitted operating program or algorithm via the respective lines 116, 118, 124, 126, 128.

Figure 14:
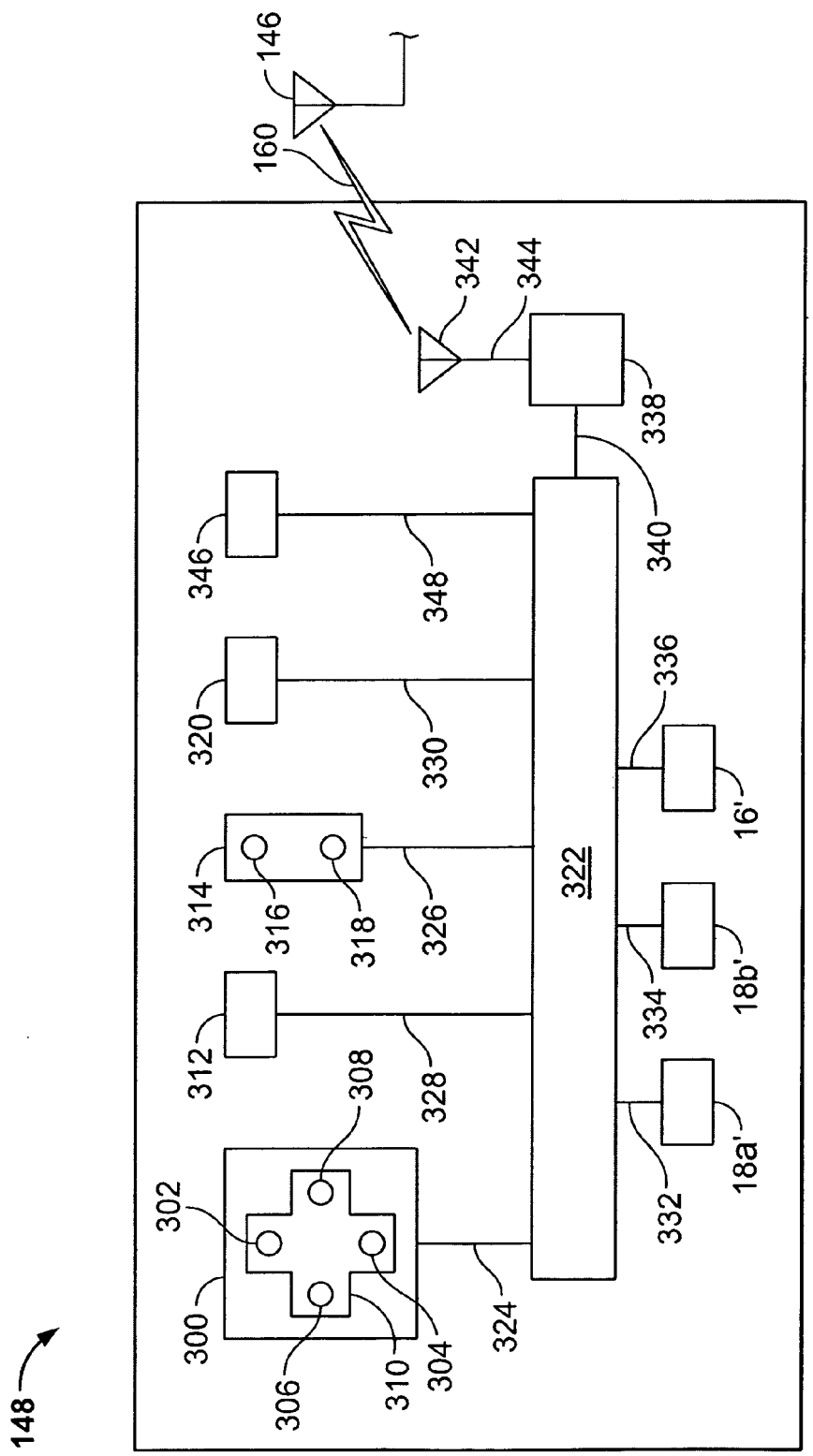
FIG. 14 is a schematic view of a wireless remote control unit of the electromechanical surgical device illustrated in FIG. 1.

Referring now to FIG. 14, there is seen a schematic view of a wireless RCU 148. The wireless RCU 148 includes a steering controller 300 having a plurality of switches 302, 304, 306, 308 arranged under a four-way rocker 310. The operation of the switches 302, 304, via the rocker 310, controls the operation of the first and second steering cables 34, 35 via the third motor 84. Similarly, the operation of the switches 306, 308, via the rocker 310, controls the operation of the third and fourth steering cables 36, 37 via the fourth motor 92. It should be appreciated that the rocker 310 and the switches 302, 304, 306, 308 are arranged so that the operation of the switches 302, 304 steers the flexible shaft 20 in the north-south direction and that the operation of the switches 306, 308 steers the flexible shaft 20 in the east-west direction. Reference herein to north, south, east and west is made to a relative coordinate system. Alternatively, a digital joystick, analog joystick, etc. may be provided in place of the rocker 310 and the switches 302, 304, 306, 308. Potentiometers or any other type of actuator may also be used in place of the switches 302, 304, 306, 308.

The wireless RCU 148 further includes a steering engage/disengage switch 312, the operation of which controls the operation of the fifth motor 96 to selectively engage and disengage the steering mechanism. The wireless RCU 148 also includes a two-way rocker 314 having first and second switches 316, 318 operable thereby. The operation of these switches 316, 318 controls certain functions of the electromechanical surgical device 10 and any surgical instrument or attachment attached to the flexible shaft 20 in accordance with the operating program or algorithm corresponding to the attached surgical instrument or attachment, if any. For example, where the surgical instrument is a circular surgical stapler attachment, operation of the two-way rocker 314 may control the advancement and retraction of an anvil. The wireless RCU 148 is provided with yet another switch 320, the operation of which may further control the operation of the electromechanical surgical device 10 and any surgical instrument or attachment attached to the flexible shaft 20 in accordance with the operating program or algorithm corresponding to the attached surgical instrument or attachment, if any. For example, when the circular surgical stapler attachment is attached to the flexible shaft 20, operation of the switch 320 initiates the advancement, or firing sequence, of the staple driver/cutter.

The wireless RCU 148 includes a controller 322, which is electrically and logically connected with the switches 302, 304, 306, 308 via line 324, with the switches 316, 318 via line 326, with the switch 312 via line 328 and with the switch 320 via line 330. The wireless RCU 148 may include indicators 18a', 18b', corresponding to the indicators 18a, 18b of front panel 15, and a display device 16', corresponding to the display device 16 of the front panel 15. If provided, the indicators 18a', 18b' are electrically and logically connected to the controller 322 via respective lines 332, 334, and the display device 16' is electrically and logically connected to the controller 322 via the line 336. The controller 322 is electrically and logically connected to a transceiver 338 via line 340, and the transceiver 338 is electrically and logically connected to a receiver/transmitter 342 via line 344. A power supply, not shown, for example, a battery, may be provided in the wireless RCU 148 to power the same. Thus, the wireless RCU 148 may be used to control the operation of the electromechanical surgical device 10 and any surgical instrument or attachment attached to the flexible shaft 20 via a wireless link 160.

The wireless RCU 148 may include a switch 346 connected to the controller 322 via line 348. Operation of the switch 346 transmits a data signal to the transmitter/receiver 146 via the wireless link 160. The data signal includes identification data uniquely identifying the wireless RCU 148. This identification data is used by the controller 122 to prevent unauthorized operation of the electromechanical surgical device 10 and to prevent interference with the operation of the electromechanical surgical device 10 by another wireless RCU. Each subsequent communication between the wireless RCU 148 and the electromechanical device surgical 10 may include the identification data. Thus, the controller 122 can discriminate between wireless RCUs and thereby allow only a single, identifiable wireless RCU 148 to control the operation of the electromechanical surgical device 10 and any surgical instrument or attachment attached to the flexible shaft 20.

Based on the positions of the components of the surgical instrument or attachment attached to the flexible shaft 20, as determined in accordance with the output signals from the quadrature rings 2080, the controller 122 may selectively enable or disable the functions of the electromechanical surgical device 10 as defined by the operating program or algorithm corresponding to the attached surgical instrument or attachment. For example, where the surgical instrument or attachment is a circular surgical stapler attachment, the firing function controlled by the operation of the switch 320 may be disabled unless the space or gap between an anvil and a body portion is determined to be within an acceptable range. The space or gap between the anvil and the body portion is determined based on the output signal from the quadrature rings 2080, as more fully described hereinabove. It should be appreciated that the switch 320 itself remains operable but that the controller 122 does not effect the corresponding function unless the space or gap is determined to be within the acceptable range. Also, the firing function controlled by the operation of the switch 320 may be disabled if moisture is detected within the flexible shaft 20 by the moisture sensor 990.

Figure 15:
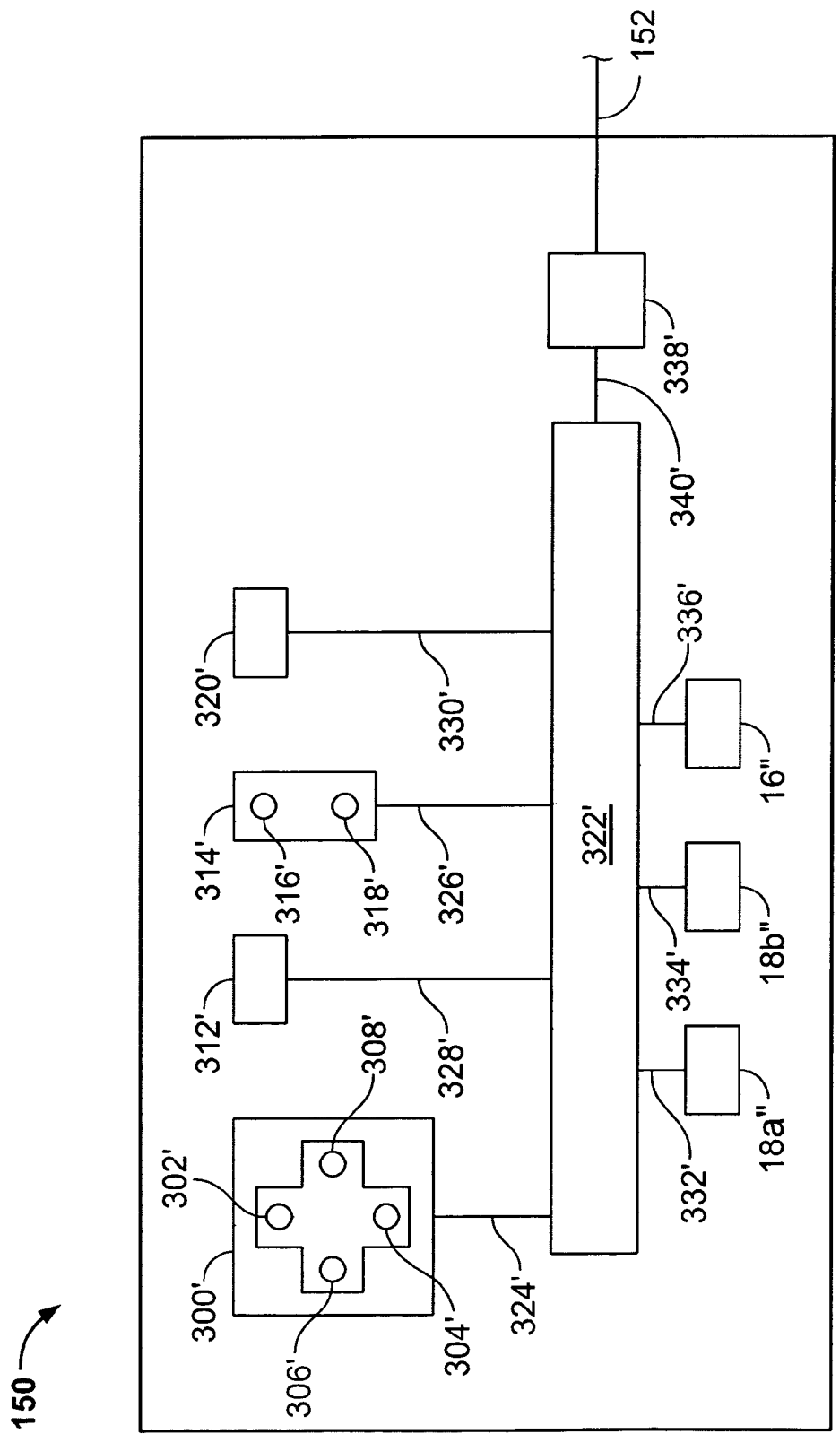
FIG. 15 is a schematic view of a wired remote control unit of the electromechanical surgical device illustrated in FIG. 1.

Referring now to FIG. 15, there is seen a schematic view of a wired RCU 150. In the example embodiment, the wired RCU 150 includes substantially the same control elements as the wireless RCU 148 and further description of such elements is omitted. Like elements are noted in FIG. 15 with an accompanying prime. It should be appreciated that the functions of the electromechanical surgical device 10 and any surgical instrument or attachment attached to the flexible shaft 20 may be controlled by the wired RCU 150 and/or by the wireless RCU 148. In the event of a battery failure, for example, in the wireless RCU 148, the wired RCU 150 may be used to control the functions of the electromechanical surgical device 10 and any surgical instrument or attachment attached to the flexible shaft 20.

As described hereinabove, the front panel 15 of the housing 14 includes the display device 16 and the indicators 18a, 18b. The display device 16 may include an alpha-numeric display device, such as an LCD display device. The display device 16 may also include an audio output device, such as a speaker, a buzzer, etc. The display device 16 is operated and controlled by the controller 122 in accordance with the operating program or algorithm corresponding to a surgical instrument or attachment, if any, attached to the flexible shaft 20. If no surgical instrument or attachment is so attached, a default operating program or algorithm may be read or selected by, or transmitted to, the controller 122 to thereby control the operation of the display device 16 as well as the other aspects and functions of the electromechanical surgical device 10. If a circular surgical stapler attachment is attached to flexible shaft 20, the display device 16 may display, for example, data indicative of the gap between the anvil and the body portion as determined in accordance with the output signal of quadrature rings 2080, as more fully described hereinabove.

Similarly, the indicators 18a, 18b are operated and controlled by the controller 122 in accordance with the operating program or algorithm corresponding to the surgical instrument or attachment, if any, attached to the flexible shaft 20. The indicator 18a and/or the indicator 18b may include an audio output device, such as a speaker, a buzzer, etc., and/or a visual indicator device, such as an LED, a lamp, a light, etc. If a circular surgical stapler attachment is attached to the flexible shaft 20, the indicator 18a may indicate, for example, that the electromechanical surgical device 10 is in a power ON state, and the indicator 18b may, for example, indicate whether the gap between the anvil and the body portion is determined to be within the acceptable range as more fully described hereinabove. It should be appreciated that although only two indicators 18a, 18b are described, any number of additional indicators may be provided as necessary. Additionally, it should be appreciated that although a single display device 16 is described, any number of additional display devices may be provided as necessary.

The display device 16' and the indicators 18a', 18b' of the wireless RCU 150 and the display device 16" and the indicators 18a", 18b" of the wired RCU 148 are similarly operated and controlled by the respective controller 322, 322' in accordance with the operating program or algorithm corresponding to the surgical instrument or attachment, if any, attached to the flexible shaft 20.

What is claimed is:

1. A surgical instrument including a shaft having an elongated outer sheath, an anvil, and a staple/driver cutter, the surgical instrument comprising:

a plurality of rotatable drive shafts disposed within the outer sheath, each of the plurality of rotatable drive shafts configured to rotate at a selectable speed setting and a selectable torque setting; and a quadrature ring having two tabs and two phototransistors, the two tabs mounted on at least one rotatable drive shaft of the plurality of rotatable drive shafts, the two tabs extending radially from and configured to rotate with the at least one rotatable drive shaft of the plurality of rotatable drive shafts, and the two phototransistors mounted proximal to the two tabs of the quadrature ring and within the outer sheath arranged approximately 90 degrees from each other relative to an axis of the at least one rotatable drive shaft of the plurality of rotatable drive shafts and a plurality of light sources mounted distal to the two tabs and within the outer sheath, wherein, upon rotation of the at least one rotatable drive shaft of the plurality of rotatable drive shafts, the two tabs alternately block and allow light from each of the plurality of light sources to be detected by the two phototransistors to permit the quadrature ring to determine angular position and rotational direction of the at least one rotatable drive shaft of the plurality of rotatable drive shafts based on one-quarter-revolution increments;

wherein the angular position and rotational direction determined by the quadrature ring facilitate determination of a relative displacement of the anvil with respect to the staple/driver cutter.

2. The surgical instrument according to claim 1, wherein each of the plurality of light sources is mounted at a distal end of the shaft.

3. The surgical instrument according to claim 1, wherein the shaft is flexible.

4. The surgical instrument according to claim 1, wherein the shaft is rigid.

5. The surgical instrument according to claim 1, wherein the shaft is articulable.

6. The surgical instrument according to claim 1, wherein the shaft is articulatable.

7. The surgical instrument according to claim 1, wherein each of the plurality of light sources is a light-emitting diode.

8. The surgical instrument according to claim 7, wherein the outer sheath is autoclavable.

9. The surgical instrument according to claim 7, wherein the outer sheath includes a fluoropolymer/silicone material.

10. The surgical instrument according to claim 1, further comprising at least one fiber optic cable for transmitting light from each of the plurality of light sources.

11. The surgical instrument according to claim 10, wherein the two tabs of the quadrature ring and the plurality of light sources are configured such that light transmitted from each of the plurality of light sources is interpretable by a controller in order to determine the rotation of the at least one rotatable drive shaft of the plurality of rotatable drive shafts.

12. The surgical instrument according to claim 11, wherein the controller is disposed within a remote power console.

13. The surgical instrument according to claim 12, further comprising a first coupling at a proximal end of the shaft, the first coupling being configured to detachably couple the shaft to the remote power console.

14. The surgical instrument according to claim 13, further comprising a second coupling connected to a distal end of the outer sheath configured to detachably couple to a surgical attachment.

15. The surgical instrument according to claim 14, wherein the controller is configured to determine a position of a component of the surgical attachment based upon an interpretation of the transmitted light.

16. The surgical instrument according to claim 1, further comprising a moisture sensor disposed within the outer sheath configured to detect moisture within the outer sheath.

17. The surgical instrument according to claim 1, further comprising a memory unit disposed in the shaft.

18. The surgical instrument according to claim 17, wherein the memory unit stores data including at least one of serial number data, identification data or usage data.

19. The surgical instrument according to claim 18, further comprising a data transfer cable disposed within the shaft, wherein the memory unit is logically and electrically connected to the data transfer cable.

20. A surgical instrument including a shaft having an elongated outer sheath, an anvil, and a staple/driver cutter, the surgical instrument comprising:
 a plurality of rotatable drive shafts disposed within the outer sheath, each of the plurality of rotatable drive shafts configured to rotate at a selectable speed setting and a selectable torque setting;
 a plurality of light sources mounted at a distal position within the outer sheath;
 a quadrature ring having two tabs mounted on at least one rotatable shaft of the plurality of rotatable drive shafts, the two tabs extending radially from and configured to rotate with the at least one rotatable drive shaft of the plurality of rotatable drive shafts; and
 at least one fiber optic cable extending along the length of the elongated outer sheath and configured to transmit light received from each of the plurality of light sources at the distal position within the outer sheath to a proximal position within the outer sheath, wherein, upon rotation of the at least one rotatable drive shaft of the plurality of rotatable drive shafts, the two tabs of the quadrature ring alternately block and allow light from each of the plurality of light sources to be received and transmitted by the at least one fiber optic cable to permit the quadrature ring to determine angular position and rotational direction of the at least one rotatable drive shaft of the plurality of rotatable drive shafts based on one-quarter-revolution increments;
 wherein the angular position and rotational direction determined by the quadrature ring facilitate determination of a relative displacement of the anvil with respect to the staple/driver cutter.

* * * * *